United States Patent
Oh et al.

(10) Patent No.: US 10,278,674 B2
(45) Date of Patent: May 7, 2019

(54) ULTRASOUND APPARATUS AND METHOD OF DISPLAYING ULTRASOUND IMAGES

(71) Applicant: SAMSUNG MEDISON CO., LTD., Hongcheon-gun (KR)

(72) Inventors: Dong-hoon Oh, Hongcheon-gun (KR); Ki-sang Yoon, Hongcheon-gun (KR); Dong-gyu Hyun, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 0 days.

(21) Appl. No.: 15/148,037

(22) Filed: May 6, 2016

(65) Prior Publication Data

US 2017/0164928 A1 Jun. 15, 2017

(30) Foreign Application Priority Data

Dec. 10, 2015 (KR) .......................... 10-2015-0176030

(51) Int. Cl.
*A61B 8/08* (2006.01)
*G06T 15/08* (2011.01)
*A61B 8/00* (2006.01)

(52) U.S. Cl.
CPC .............. *A61B 8/463* (2013.01); *A61B 8/466* (2013.01); *A61B 8/469* (2013.01); *A61B 8/483* (2013.01); *A61B 8/5207* (2013.01); *G06T 15/08* (2013.01)

(58) Field of Classification Search
None
See application file for complete search history.

(56) References Cited

U.S. PATENT DOCUMENTS

| 8,103,066 B2 | 1/2012 | Kim et al. |
| 8,403,854 B2 | 3/2013 | Sasaki |
| 8,810,568 B2 | 8/2014 | Tian et al. |
| 2013/0235032 A1* | 9/2013 | Kim ........................ G06T 15/08 |
| | | 345/419 |
| 2013/0331697 A1 | 12/2013 | Park et al. |
| 2014/0152656 A1 | 6/2014 | Yoo et al. |
| 2015/0116323 A1* | 4/2015 | Buckton ................. G06T 19/00 |
| | | 345/424 |
| 2016/0007972 A1 | 1/2016 | Nishiura |

(Continued)

FOREIGN PATENT DOCUMENTS

| EP | 2823764 A1 | 1/2015 |
| EP | 2898830 A1 | 7/2015 |
| JP | 2005-218520 A | 8/2005 |

(Continued)

OTHER PUBLICATIONS

Communication dated Apr. 11, 2017, issued by the European Patent Office in counterpart European Application No. 16165738.2.

*Primary Examiner* — Peter Hoang
(74) *Attorney, Agent, or Firm* — Sughrue Mion, PLLC

(57) ABSTRACT

Provided is an ultrasound diagnosis apparatus including: a display configured to display a two-dimensional (2D) ultrasound image of an object and a three-dimensional (3D) ultrasound image of a region of interest (ROI) set in the 2D ultrasound image; and a controller configured to control the display to display a region not rendered as the 3D ultrasound image from among regions in the 2D ultrasound image in such a manner that the region is distinguished from a region rendered as the 3D ultrasound image.

22 Claims, 22 Drawing Sheets

(56) References Cited

U.S. PATENT DOCUMENTS

2016/0317130 A1* 11/2016 Auvray .................. A61B 8/483

FOREIGN PATENT DOCUMENTS

| JP | 2012-65737 A | 4/2012 |
| JP | 2013-244047 A | 12/2013 |
| JP | 2015-57108 A | 3/2015 |
| KR | 10-0948047 B1 | 3/2010 |
| KR | 10-2014-0038777 A | 3/2014 |
| KR | 10-150518 B1 | 3/2015 |
| WO | 2008149291 A1 | 12/2008 |
| WO | 2014156269 A1 | 10/2014 |
| WO | 2015091368 A1 | 6/2015 |

* cited by examiner

REMOVAL TO LESSER
DEGREE THAN APPROPRIATE

REMOVAL TO GREATER
DEGREE THAN APPROPRIATE

REMOVAL TO
APPROPRIATE DEGREE

FIG. 9
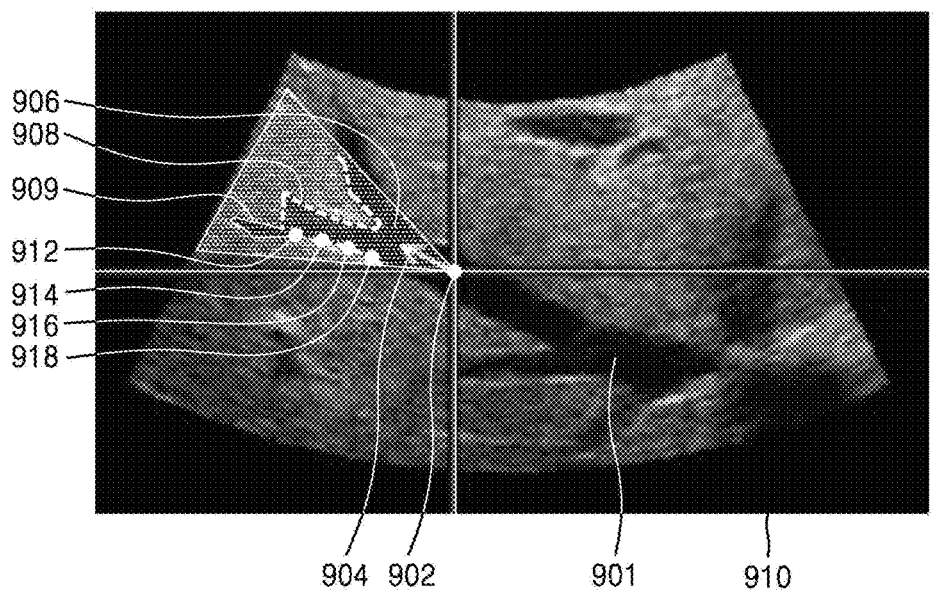
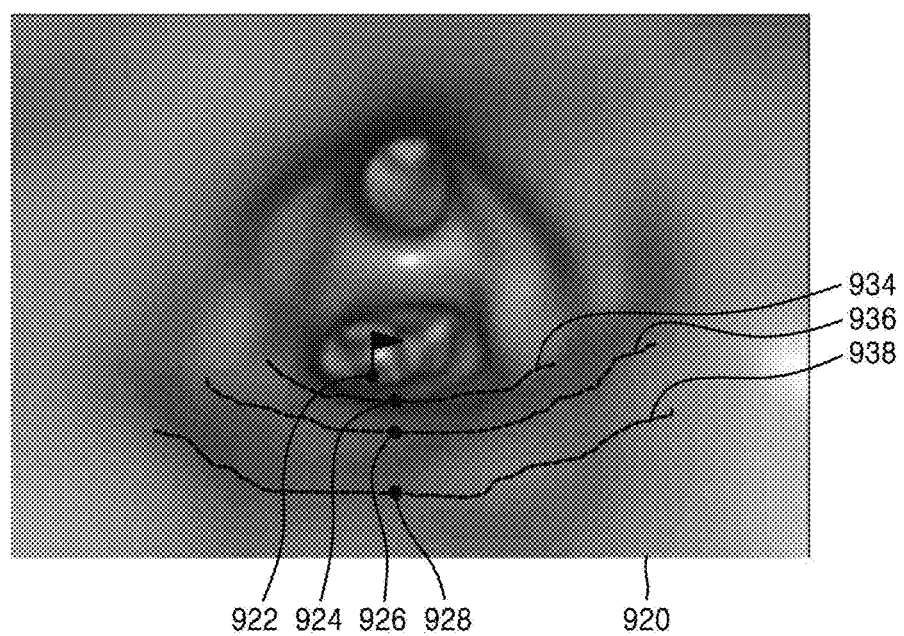

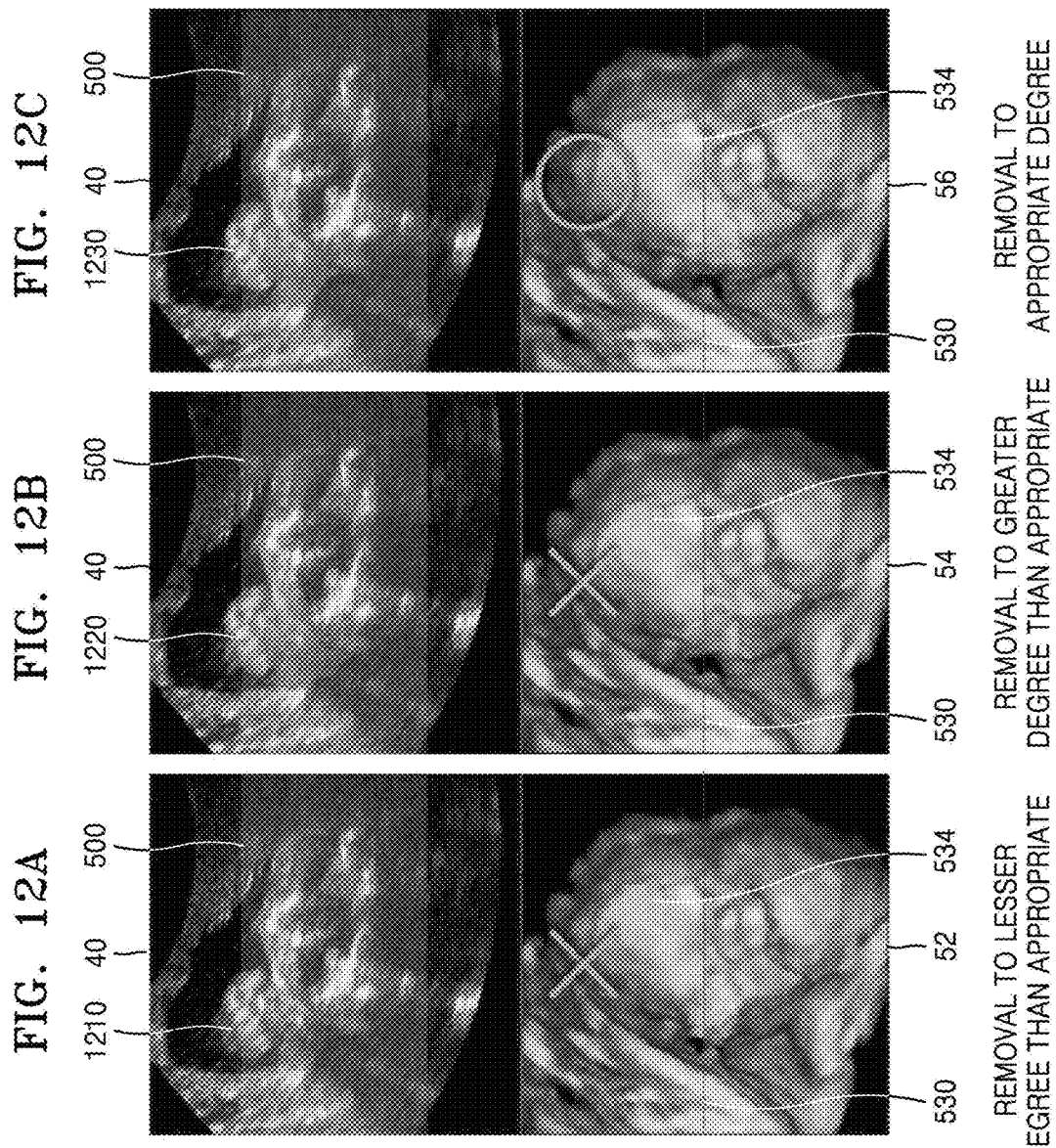

ULTRASOUND APPARATUS AND METHOD OF DISPLAYING ULTRASOUND IMAGES

CROSS-REFERENCE TO RELATED APPLICATION

This application claims the benefit of Korean Patent Application No. 10-2015-0176030, filed on Dec. 10, 2015, in the Korean Intellectual Property Office, the disclosure of which is incorporated herein in its entirety by reference.

BACKGROUND

1. Field

The present disclosure relates to methods and apparatuses for displaying a region rendered as a three-dimensional (3D) ultrasound image in such a manner as to be distinguished from a region not rendered as the 3D ultrasound image.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissue or blood flow). In particular, ultrasound diagnosis apparatuses are used for medical purposes including observing an internal area of an object, detecting foreign substances, and assessing injuries. Such ultrasound diagnosis apparatuses provide high stability, display images in real time, and are safe due to there being no radiation exposure, compared to X-ray apparatuses. Therefore, an ultrasound diagnosis apparatus is widely used together with other types of imaging diagnosis devices.

SUMMARY

Provided are methods and apparatuses for displaying a region not rendered as a three-dimensional (3D) ultrasound image from among regions in a two-dimensional (2D) ultrasound image in such a manner as to be distinguished from a region rendered as the 3D ultrasound image.

Additional aspects will be set forth in part in the description which follows and, in part, will be apparent from the description, or may be learned by practice of the presented embodiments.

According to an aspect of an embodiment, an ultrasound diagnosis apparatus includes: a display configured to display a 2D ultrasound image of an object and a 3D ultrasound image with respect to a region of interest (ROI) set in the 2D ultrasound image; and a controller configured to determine points in the 2D ultrasound image corresponding to a surface of a display volume of the object represented by the 3D ultrasound image and control the display to display the determined points on the 2D ultrasound image.

The controller may determine points on the surface of the display volume that intersect a cross-section of the object represented by the 2D ultrasound image as being the points in the 2D ultrasound image corresponding to the surface of the display volume.

The display may display a position of the surface of the display volume of the object by displaying a line connecting the determined points in the 2D ultrasound image.

The ultrasound diagnosis apparatus may further include a user input unit configured to receive a user input for adjusting a depth of the surface of the display volume, and the controller may change a position of the line as the depth of the surface of the display volume is adjusted.

The user input for adjusting the depth of the surface of the display volume may be a user input for changing a 3D rendering parameter necessary for rendering the 3D ultrasound image The user input for adjusting the depth of the surface of the display volume may be a user input for removing a part of the display volume of the object represented by the 3D ultrasound image.

The display may display on the 3D ultrasound image a position of a cross-section of the object represented by the 2D ultrasound image.

The ultrasound diagnosis apparatus may further include a user input unit configured to receive a user input for selecting a depth of starting points in the 2D ultrasound image where 3D rendering will start, and the controller may generate a 3D ultrasound image based on the selected starting points and control the display to display the generated 3D ultrasound image.

Furthermore, the controller may control the display to display points having the same depth as a depth of a starting point selected by the user, from among points in the 2D ultrasound image corresponding to a surface of a display volume of the object, in such a manner that the points having the same depth as the depth of the starting point are distinguished from points having depths different from that same depth.

Furthermore, the controller may determine points in the 3D ultrasound image corresponding to a cross-section of the object represented by the 2D ultrasound image and control the display to display points where a surface of a display volume has the same depth as a depth of a starting point selected by the user, from among the determined points, in such a manner that the points having the same depth as the depth of the starting point are distinguished from points having depths different from that same depth.

The 3D ultrasound image may be an ultrasound virtual endoscopic image.

According to an aspect of another embodiment, a method of displaying an ultrasound image includes: displaying a 2D ultrasound image of an object and a 3D ultrasound image with respect to an ROI set in the 2D ultrasound image; determining points in the 2D ultrasound image corresponding to a surface of a display volume of the object represented by the 3D ultrasound image; and displaying the determined points on the 2D ultrasound image.

Furthermore, the determining of the points in the 2D ultrasound image corresponding to the surface of the display volume of the object may include determining points on a surface of a display volume that intersect a cross-section of the object represented by the 2D ultrasound image as being the points in the 2D ultrasound image corresponding to the surface of the display volume.

Furthermore, the displaying of the determined points on the 2D ultrasound image may include displaying a position of the surface of the display volume of the object by displaying a line connecting the determined points in the 2D ultrasound image.

The method may further include receiving a user input for adjusting a depth of the surface of the display volume and changing a position of the line as the depth of the surface of the display volume is adjusted.

The user input for adjusting the depth of the surface of the display volume may be a user input for changing a 3D rendering parameter necessary for rendering the 3D ultrasound image.

The user input for adjusting the depth of the surface of the display volume may be a user input for removing a part of the display volume of the object represented by the 3D ultrasound image.

The method may further include displaying on the 3D ultrasound image a position of a cross-section of the object represented by the 2D ultrasound image.

Furthermore, the displaying of the 3D ultrasound image with respect to the ROI set in the 2D ultrasound image may include: receiving a user input for selecting a depth of starting points in the 2D ultrasound image where 3D rendering will start; generating a 3D ultrasound image based on the selected starting points; and displaying the generated 3D ultrasound image.

Furthermore, the displaying of the determined points on the 2D ultrasound image may include displaying points having the same depth as a depth of a starting point selected by the user, from among points in the 2D ultrasound image corresponding to the surface of the display volume of the object, in such a manner that the points having the same depth as the depth of the starting point are distinguished from points having depths different from that same depth.

The method may further include: determining points in the 3D ultrasound image corresponding to a cross-section of the object represented by the 2D ultrasound image; and displaying points where a surface of a display volume has the same depth as a depth of a starting point selected by the user, from among the determined points, in such a manner that the points having the same depth as the depth of the starting point are distinguished from points having depths different from that same depth.

Furthermore, the 3D ultrasound image may be an ultrasound virtual endoscopic image.

According to an aspect of another embodiment, an ultrasound diagnosis apparatus includes: a display configured to display a 2D ultrasound image of an object and a 3D ultrasound image of an ROI set in the 2D ultrasound image; and a controller configured to control the display to display a region not rendered as the 3D ultrasound image from among regions in the 2D ultrasound image in such a manner that the region is distinguished from a region rendered as the 3D ultrasound image.

The display may display the region rendered as the 3D ultrasound image in such a manner as to be distinguished from the region not rendered as the 3D ultrasound image by displaying, on the 2D ultrasound image, points in the 2D ultrasound image corresponding to a surface of a display volume of the object represented by the 3D ultrasound image.

The controller may determine points on the surface of the display volume that intersect a cross-section of the object represented by the 2D ultrasound image as being the points in the 2D ultrasound image corresponding to the surface of the display volume.

The controller may determine the region not rendered as the 3D ultrasound image in the ROI, and the display may display the region rendered as the 3D ultrasound image in such a manner as to be distinguished from the region not rendered as the 3D ultrasound image by displaying the non-rendered region on the 2D ultrasound image.

The ultrasound diagnosis apparatus may further include a user input unit configured to receive a user input for adjusting a depth of a surface of a display volume of the object represented by the 3D ultrasound image, and the controller may change the non-rendered region as the depth of the surface of the display volume is adjusted and control the display to display the changed non-rendered region.

The user input for adjusting the depth of the surface of the display volume may be a user input for changing a 3D rendering parameter necessary for rendering the 3D ultrasound image.

The user input for adjusting the depth of the surface of the display volume may be a user input for removing a part of the display volume of the object represented by the 3D ultrasound image.

The display may display on the 3D ultrasound image a position of a cross-section of the object represented by the 2D ultrasound image.

The ultrasound diagnosis apparatus may further include a user input unit configured to receive a user input for setting the ROI in the 2D ultrasound image, and the controller may generate a 3D ultrasound image based on the set ROI and control the display to display the generated 3D ultrasound image.

The 3D ultrasound image may be an ultrasound virtual endoscopic image of the ROI set in the 2D ultrasound image, and the display may display a region that has been rendered as the ultrasound virtual endoscopic image from among the regions in the 2D ultrasound image in such a manner that the region is distinguished from a region that has never been rendered as the ultrasound virtual endoscopic image.

According to an aspect of another embodiment, a method of displaying an ultrasound image includes: displaying a 2D ultrasound image of an object and a 3D ultrasound image of an ROI set in the 2D ultrasound image; and displaying a region not rendered as the 3D ultrasound image from among regions in the 2D ultrasound image in such a manner that the region is distinguished from a region rendered as the 3D ultrasound image.

The displaying of the region not rendered as the 3D ultrasound image in such a manner as to be distinguished from the region rendered as the 3D ultrasound image may include displaying, on the 2D ultrasound image, points in the 2D ultrasound image corresponding to a surface of a display volume of the object represented by the 3D ultrasound image.

The displaying of the points in the 2D ultrasound image corresponding to the surface of the display volume of the object represented by the 3D ultrasound image may include determining points on the surface of the display volume that intersect a cross-section of the object represented by the 2D ultrasound image as being the points in the 2D ultrasound image corresponding to the surface of the display volume.

The displaying of the region not rendered as the 3D ultrasound image in such a manner as to be distinguished from the region rendered as the 3D ultrasound image may include determining the region not rendered as the 3D ultrasound image in the ROI and displaying the non-rendered region on the 2D ultrasound image.

The method may further include: receiving a user input for adjusting a depth of a surface of a display volume of the object represented by the 3D ultrasound image; and changing the non-rendered region as the depth of the surface of the display volume is adjusted and displaying the changed non-rendered region The method may further include displaying on the 3D ultrasound image a position of a cross-section of the object represented by the 2D ultrasound image.

The method may further include: receiving a user input for setting the ROI in the 2D ultrasound image; generating a 3D ultrasound image based on the set ROI; and displaying the generated 3D ultrasound image.

The 3D ultrasound image may be an ultrasound virtual endoscopic image of the ROI set in the 2D ultrasound image, and the method may further include displaying a region that has been rendered as the ultrasound virtual endoscopic image from among the regions in the 2D ultrasound image in such a manner that the region is distinguished from a region that has never been rendered as the ultrasound virtual endoscopic image.

BRIEF DESCRIPTION OF THE DRAWINGS

These and/or other aspects will become apparent and more readily appreciated from the following description of the embodiments, taken in conjunction with the accompanying drawings in which:

FIG. 9 illustrates an example in which an ultrasound diagnosis apparatus displays, on a 2D ultrasound image, a position of a surface of a display volume represented by an ultrasound virtual endoscopic image, according to an embodiment;

FIGS. 12A through 12C illustrate examples in which an ultrasound diagnosis apparatus displays, on a 2D ultrasound image, a region not rendered as a 3D ultrasound image from among regions in the 2D ultrasound image, according to another embodiment;

DETAILED DESCRIPTION

Figure 1A:
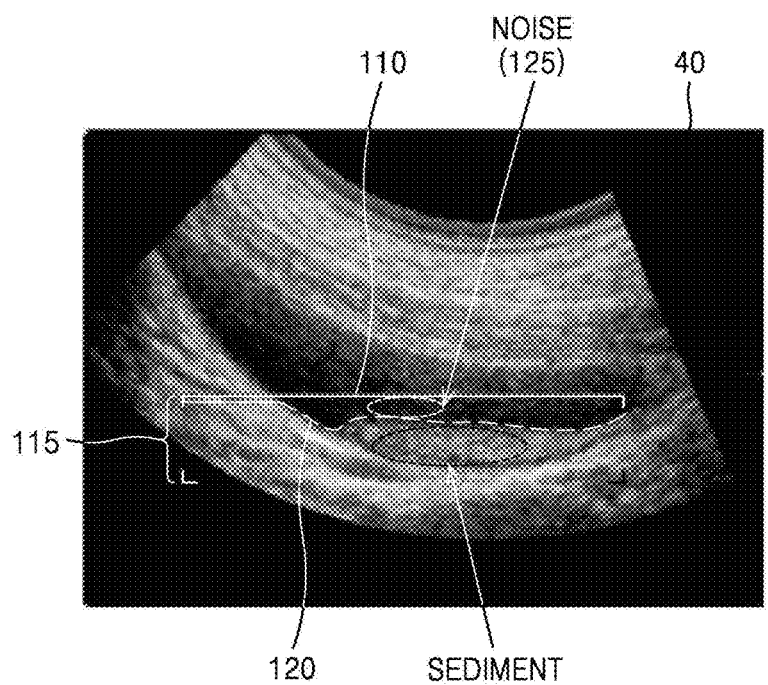
FIGS. 1A and 1B illustrate an example in which an ultrasound diagnosis apparatus displays a position of a surface of a display volume represented by a three-dimensional (3D) ultrasound image on a two-dimensional (2D) ultrasound image, according to an embodiment.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the inventive concept.

When a part "includes" or "comprises" an element, unless there is a particular description contrary thereto, the part can further include other elements, not excluding the other elements. In addition, terms such as " . . . unit", " . . . module", or the like refer to units that perform at least one function or operation, and the units may be implemented as hardware or software or as a combination of hardware and software.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. In addition, parts not related to the present inventive concept are omitted to clarify the description of embodiments. Expressions such as "at least one of," when preceding a list of elements, modify the entire list of elements and do not modify the individual elements of the list.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the uterus, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "two-dimensional (2D) ultrasound image" may mean an ultrasound image showing a cross-section of an object.

Throughout the specification, a "three-dimensional (3D) ultrasound image" may mean an ultrasound image showing a 3D region of an object. A 3D ultrasound image may be generated by producing volume data with respect to a 3D region of an object based on echo signals received from the 3D region of the object and performing volume rendering with respect to the generated volume data.

A 3D ultrasound image may be an ultrasound image showing a surface of a 3D region of the object or an ultrasound image showing an internal structure of a 3D region of the object, according to types of rendering techniques used.

Throughout the specification, a "user" may be, but is not limited to, a medical expert, for example, a medical doctor, a nurse, a medical laboratory technologist, or a medical imaging expert, or a technician who repairs medical apparatuses.

Hereinafter, embodiments will be described in detail with reference to the accompanying drawings.

Figure 1B:
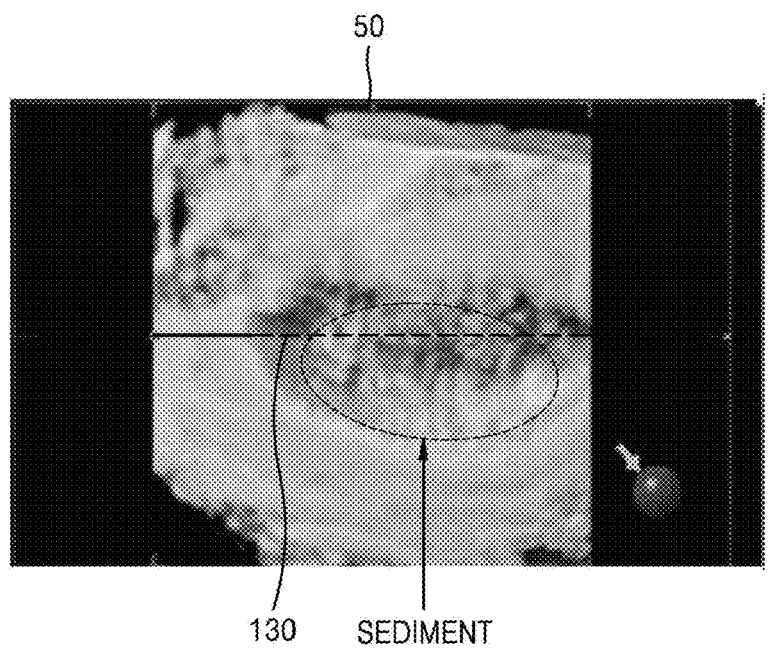

FIGS. 1A and 1B illustrate an example in which an ultrasound diagnosis apparatus (1000 of FIG. 17 or 18) displays a position of a surface of a display volume represented by a 3D ultrasound image on a 2D ultrasound image, according to an embodiment.

Referring to FIGS. 1A and 1B, the ultrasound diagnosis apparatus 1000 may display on a 2D ultrasound image 40 a position of a surface of a display volume represented by a 3D ultrasound image 50 of an object.

Referring to FIG. 1A, the ultrasound diagnosis apparatus 1000 may display the 2D ultrasound image 40 showing a patient's gallbladder. The ultrasound diagnosis apparatus 1000 may receive a user input for setting a region of interest (ROI) 110 to be displayed as the 3D ultrasound image 50 in the 2D ultrasound image 40. For example, the ultrasound diagnosis apparatus 1000 may receive a user input for selecting points 110 where 3D rendering will start. Furthermore, the ultrasound diagnosis apparatus 1000 may receive a user input for selecting a depth 115 of a volume to be represented as a 3D ultrasound image. Regions respectively defined by the selected points 110 and the selected depth 115 may be referred to as ROIs 110 and 115.

Referring to FIG. 1B, when the user inputs for respectively setting the ROIs 110 and 115 are received, the ultrasound diagnosis apparatus 1000 may display the 3D ultrasound image 50 with respect to the set ROIs 110 and 115.

The ultrasound diagnosis apparatus 1000 may determine an intensity of an ultrasound echo signal received from a first point of an object as a value of a 3D voxel corresponding to the first point. Once each voxel value is determined, the ultrasound diagnosis apparatus 1000 may determine an opacity value for each voxel value by using a transfer function (e.g., an opacity transfer function). The transfer function may be a function that takes a voxel as input and produces an opacity value as output. For example, the transfer function may be a function that maps voxel values of 0 to 255 to opacity values of 0 to 255 so that an opacity value is proportional to a voxel value. After an opacity value is determined for each voxel, the ultrasound diagnosis apparatus 1000 may accumulate opacity values for voxels along a virtual ray based on a volume rendering algorithm such as ray-casting, thereby producing the 3D ultrasound image 50 representing a 3D region of the object.

In this case, the ultrasound diagnosis apparatus 1000 may display a position of a surface of a display volume represented by the 3D ultrasound image 50 on the 2D ultrasound image 40.

Sediment may be accumulated in a patient's gallbladder as shown in FIG. 1A. To allow a user to observe a shape, size, or geometry, the ROIs 110 and 115 containing sediment may be displayed as the 3D ultrasound image 50. In this case, a noise object 125 may be present on the sediment. When the noise object 125 is present on the sediment, a surface of a display volume represented by the 3D ultrasound image 50 may be the noise object 125 that is not the sediment. As shown in FIGS. 1A and 1B, the noise object 125 is distinguishable from sediment or gallbladder tissue in the 2D ultrasound image 40 but may be difficult to distinguish therefrom in the 3D ultrasound image 50.

The ultrasound diagnosis apparatus 1000 may receive a user input for removing the noise object 125.

For example, the ultrasound diagnosis apparatus 1000 may receive a user input for deleting a region that is not to be rendered as the 3D ultrasound image 50 during volume rendering. In detail, the ultrasound diagnosis apparatus 1000 may receive a user input for cutting out the noise object 125 in the 3D ultrasound image 50. When the user input for cutting out the noise object 125 is received, the ultrasound diagnosis apparatus 1000 may set an opacity value of a voxel corresponding to the noise object 125 to "0".

When an opacity value of a voxel corresponding to the noise object 125 is set to 0, the ultrasound diagnosis apparatus 1000 may not render the noise object 125 as the 3D ultrasound image 50. Thus, the ultrasound diagnosis apparatus 1000 may display the 3D ultrasound image 50 showing sediment as a surface of a display volume.

However, even in this case, when a surface of a display volume is cut out, since it is hard to distinguish the noise object 125 from sediment or gallbladder tissue in the 3D ultrasound image 50, the user has difficulty in identifying whether a depth to which the surface of the display volume is cut out is a desired depth, i.e., whether the noise object 125 has been removed, by simply viewing the 3D ultrasound image 50.

The ultrasound diagnosis apparatus 1000 may display a position of a surface of a display volume represented by the 3D ultrasound image 50 of an object on the 2D ultrasound image 40. Since the noise object 125 is distinguishable from sediment or gallbladder tissue in the 2D ultrasound image 40, displaying the position of the surface of the display volume on the 2D ultrasound image 40 allows the user to identify whether the depth to which the surface of the display volume is cut out is a desired depth.

For example, referring back to FIG. 1A, the ultrasound diagnosis apparatus 1000 may display on the 2D ultrasound image 40 a position of a surface of a display volume represented by the 3D ultrasound image 50 as a line 120.

After the surface of the display volume has been cut out from the 3D ultrasound image 50 based on the user input, the ultrasound diagnosis apparatus 1000 may display a position of the surface of the display volume by lowering points corresponding to a cut region on the displayed line 120 by the depth to which the surface of the display volume is cut out. For example, if the display volume contains the noise object 125, the ultrasound diagnosis apparatus 1000 may display the line 120 representing the position of the surface of the display volume on the ultrasound image 40 so that the line 120 passes over the noise object 125. Furthermore, when 3D data with respect to the noise object 125 is excluded during 3D rendering based on a user input, the ultrasound diagnosis apparatus 1000 may display the line 120 representing the position of the surface of the display volume on the 2D ultrasound image 40 so that the line 120 passes beneath the noise object 125.

Furthermore, the ultrasound diagnosis apparatus 1000 may display on the 3D ultrasound image 50 the line 130 representing a position of a cross-section of the object represented by the 2D ultrasound image 40, thereby allowing the user to identify a position on the 3D ultrasound image 50 corresponding to the cross-section of the object.

Figure 2:
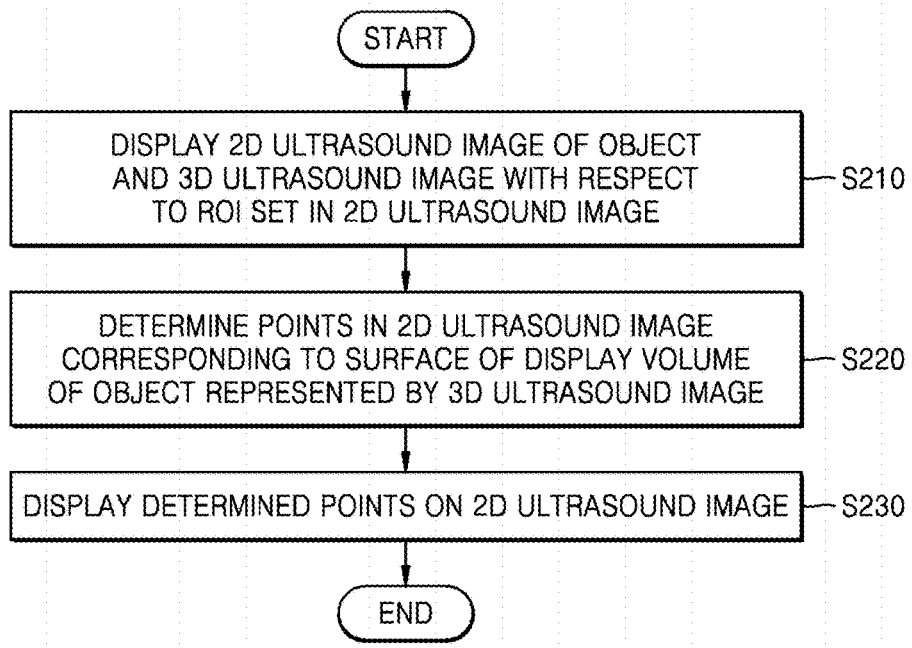
FIG. 2 is a flowchart of a method, performed by an ultrasound diagnosis apparatus, of displaying a position of a surface of a display volume represented by a 3D ultrasound image on a 2D ultrasound image, according to an embodiment.

FIG. 2 is a flowchart of a method, performed by the ultrasound diagnosis apparatus 1000, of displaying on a 2D ultrasound image a position of a surface of a display volume represented by a 3D ultrasound image, according to an embodiment.

The ultrasound diagnosis apparatus 1000 may display a 2D ultrasound image of an object and a 3D ultrasound image thereof showing an ROI set in the 2D ultrasound image (S210).

The ultrasound diagnosis apparatus 1000 may receive a user input for setting an ROI in the 2D ultrasound image. For example, the ultrasound diagnosis apparatus 1000 may receive a user input for displaying a 3D image as well as a user input for setting an ROI to be displayed as a 3D region.

When a user input for setting an ROI to be displayed as a 3D region is received, the ultrasound diagnosis apparatus 1000 may perform a 3D scan on the ROI in order to generate a 3D image.

As the 3D scan is performed on the ROI, the ultrasound diagnosis apparatus 1000 may generate 3D ultrasound data based on a received echo signal and display a 3D image based on the generated 3D ultrasound data.

Furthermore, according to an embodiment, the ultrasound diagnosis apparatus 1000 may receive 3D ultrasound data from an external device or have the 3D ultrasound data prestored therein.

The ultrasound diagnosis apparatus 1000 may determine points in the 2D ultrasound image corresponding to a surface of a display volume of the object represented by the 3D ultrasound image (S220).

For example, the ultrasound diagnosis apparatus 1000 may determine points on the surface of the display volume, which intersect a cross-section of the object represented by the 2D ultrasound image, as being points in the 2D ultrasound image corresponding to the surface of the display volume.

For example, the ultrasound diagnosis apparatus 1000 may determine positions of voxels) in a surface of a display volume as well as positions of voxels in a cross-section of the object represented by the 2D ultrasound image. The ultrasound diagnosis apparatus 1000 may determine, based on the determined positions of the voxels in the surface of the display volume and in the cross-section of the object represented by the 2D ultrasound image, points on the surface of the display volume that intersect the cross-section of the object.

The ultrasound diagnosis apparatus 1000 may display the determined points on the 2D ultrasound image (S230).

The ultrasound diagnosis apparatus 1000 may display a position of the surface of the display volume represented by the 3D ultrasound image on the 2D ultrasound image.

The ultrasound diagnosis apparatus 1000 may determine points in the 2D ultrasound image corresponding to a position of a surface of a display volume of the object represented by the 3D ultrasound image. For example, the ultrasound diagnosis apparatus 1000 may determine points in the 2D ultrasound image corresponding to a position of the surface of the display volume of the object represented by the 3D ultrasound image based on positions of voxels corresponding to points on the surface of the display volume that intersect a cross-section of the object represented by the 2D ultrasound image, which are determined in operation S220.

The ultrasound diagnosis apparatus 1000 may display a marker indicating the surface of the display volume on the determined points in the 2D ultrasound image. The ultrasound diagnosis apparatus 1000 may display as a line a position of the surface of the display volume represented by the 3D ultrasound image. Furthermore, the ultrasound diagnosis apparatus 1000 may display on the 2D ultrasound image a position of the surface of the display volume represented by the 3D ultrasound image as a dot, a line, a plane, a geometrical shape, a color, transparency, a text, or a combination of at least two thereof.

Furthermore, the ultrasound diagnosis apparatus 1000 may receive a user input for adjusting a depth of the surface of the display volume. As the depth of the surface of the display volume is adjusted, the ultrasound diagnosis apparatus 1000 may change a position of a marker indicating the surface of the display volume.

The user input for adjusting the depth of the surface of the display volume may be a user input for changing a 3D rendering parameter necessary for rendering the 3D ultrasound image. Furthermore, the user input may be a user input for removing a part of the display volume represented by the 3D ultrasound image.

Furthermore, the ultrasound diagnosis apparatus 1000 may display on the 3D ultrasound image a position of the cross-section of the object represented by the 2D ultrasound image.

Furthermore, according to an embodiment, the 3D ultrasound image may be a 3D virtual endoscopic image.

Figure 3A:
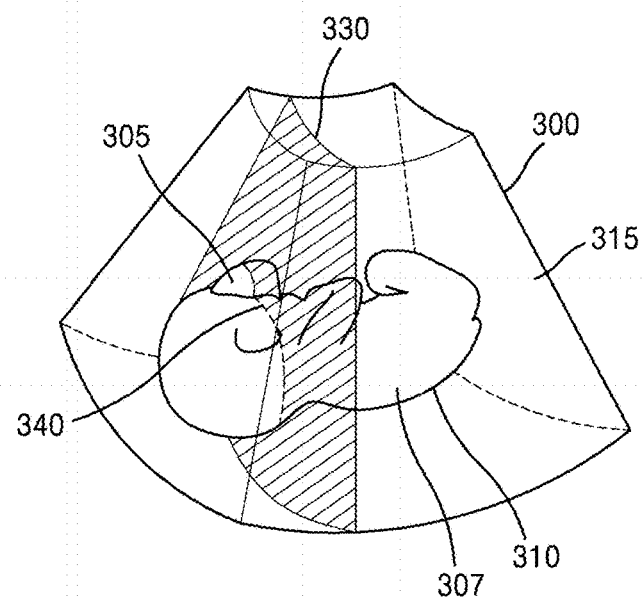
FIGS. 3A and 3B are diagrams for explaining a method, performed by an ultrasound diagnosis apparatus, of displaying a position of a surface of a display volume represented by a 3D ultrasound image on a 2D ultrasound image, according to another embodiment.
Figure 3B:
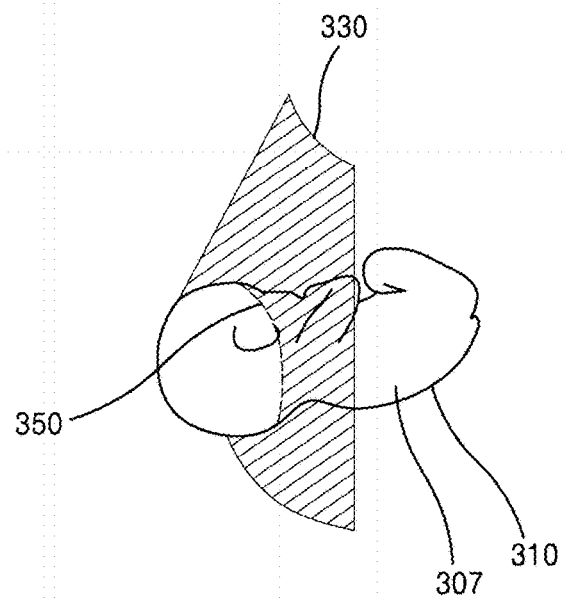

FIGS. 3A and 3B are diagrams for explaining a method, performed by the ultrasound diagnosis apparatus 1000, of displaying on a 2D ultrasound image a position of a surface of a display volume represented by a 3D ultrasound image, according to another embodiment.

Referring to FIGS. 3A and 3B, the ultrasound diagnosis apparatus 1000 may determine points in a 2D ultrasound image corresponding to a position of a surface of a display volume 310.

Referring to FIG. 3A, the ultrasound diagnosis apparatus 1000 may transmit an ultrasound signal to an uterus and obtain 3D ultrasound image data with respect to a 3D region 300 based on an ultrasound echo signal received from the uterus. The 3D region 300 may be a region scanned by an ultrasound probe and vary according to the type of a probe, an ROI set by a user, a parameter set in the ultrasound diagnosis apparatus 1000. The 3D ultrasound image data may include opacities of voxels constituting the 3D region 300.

A "display volume" of an object may be a 3D region of the object shown in a 3D ultrasound image. For example, if an ultrasound scan is performed on a fetus 307 inside the uterus, 3D ultrasound image data acquired using the ultrasound scan may include data representing the fetus 307, an amniotic fluid 315, and a placenta 305. In this case, when only the fetus 307 and the placenta 305 are depicted in a 3D ultrasound image, the display volume 310 of the object may be only regions of the fetus 307 and placenta 305 in the 3D region 300. Since different 3D ultrasound images may be displayed based on the same 3D ultrasound image data, according to a user input or a parameter set in the ultrasound diagnosis apparatus 1000, different display volumes may be represented based on the same 3D ultrasound image data. Furthermore, the "display volume" may mean 3D data represented as a 3D ultrasound image during 3D volume rendering.

A 3D ultrasound image may be a 3D representation of an ROI set in a 2D ultrasound image showing a 2D cross-section 330 of the object. Thus, the 2D cross-section 330 of the object shown in the 2D ultrasound image may be one of cross-sections constituting the 3D region 300.

The ultrasound diagnosis apparatus 1000 may determine points in the 2D ultrasound image corresponding to the surface of the display volume 310 represented by the 3D ultrasound image.

For example, the ultrasound diagnosis apparatus 1000 may determine positions of voxels in the surface of the display volume 310. Furthermore, the ultrasound diagnosis apparatus 1000 may determine positions of voxels in the 2D cross-section 330 of the object represented by the 2D ultrasound image. The ultrasound diagnosis apparatus 1000 may determine, based on the determined positions of the voxels in the surface of the display volume 310 and in the 2D cross-section 330 of the object, points 340 on the surface of the display volume 310 that intersect the 2D cross-section 330 of the object.

Furthermore, the ultrasound diagnosis apparatus 1000 may determine points in the 2D ultrasound image corresponding to a position of the surface of the display volume 310 represented by the 3D ultrasound image. For example, the ultrasound diagnosis apparatus 1000 may determine points in the 2D ultrasound image corresponding to a position of the surface of the display volume 310 of the object based on voxel positions of the points 340 on the surface of the display volume 310 that intersect the 2D cross-section 330 of the object.

As shown in FIG. 3A, when the display volume 310 of the object depicted as the 3D ultrasound image includes regions of the fetus 307 and the placenta 305, the points 340 where the surface of the display volume 310 intersects the 2D cross-section 330 may be points passing over the placenta 305. The ultrasound diagnosis apparatus 1000 may display a position of the surface of the display volume 310 on the 2D ultrasound image by displaying on the 2D ultrasound image a line connecting points passing over the placenta 305 in the 2D ultrasound image based on the determined points 340.

Referring to FIG. 3B, the ultrasound diagnosis apparatus 1000 may receive a user input for removing the placenta 305 from the display volume 310 shown in FIG. 3A. For example, if a user input for cutting out the placenta 305 from the 3D ultrasound image is received, the ultrasound diagnosis apparatus 1000 may display a 3D ultrasound image with the placenta 305 removed therefrom.

After the placenta 305 has been removed, the display volume 310 of the object represented by the 3D ultrasound image may include only the fetus 307. The ultrasound diagnosis apparatus 1000 may determine positions of points 350 where the surface of the display volume 310 intersects the 2D cross-section 330. The points 350 may pass over a head of the fetus 307. The ultrasound diagnosis apparatus 1000 may display a position of the surface of the display volume 310 on the 2D ultrasound image by displaying on the 2D ultrasound image a line connecting points passing over the head of the fetus 307 in the 2D ultrasound image based on the determined voxel positions of the points 350.

Figure 4:
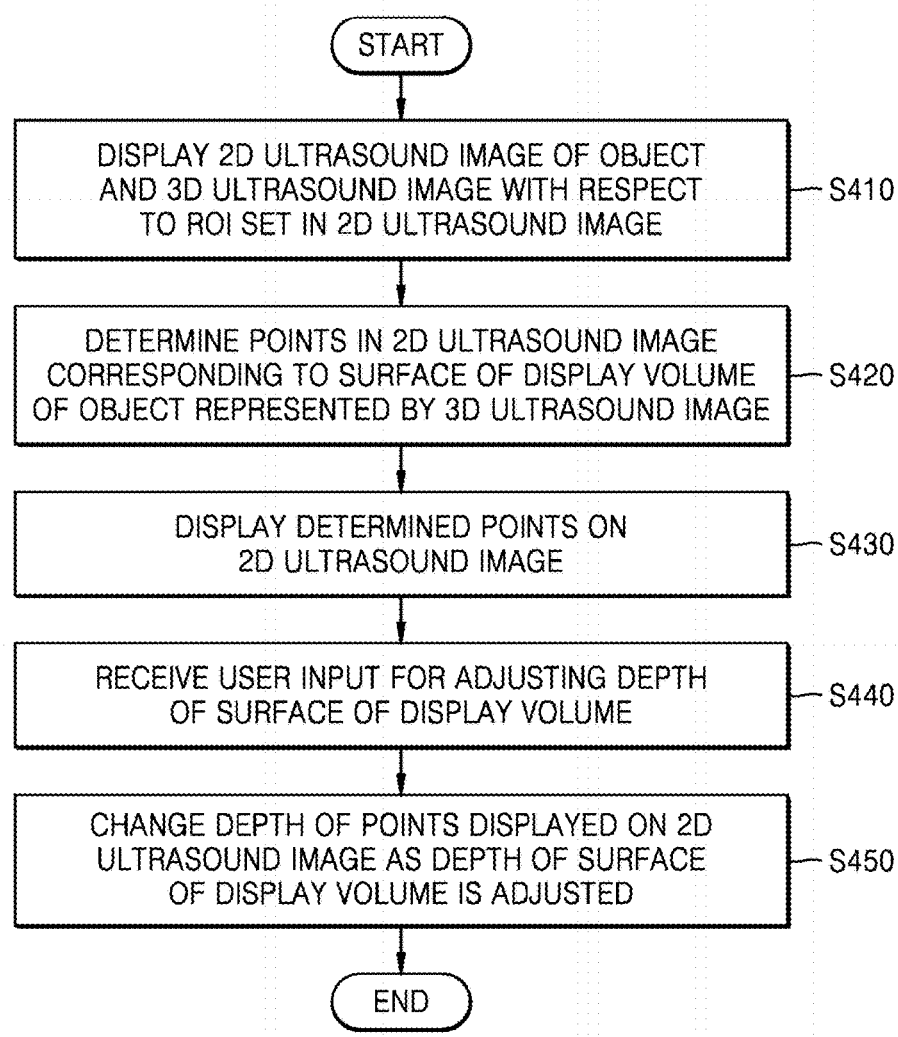
FIG. 4 is a flowchart of a method, performed by an ultrasound diagnosis apparatus, of displaying, when a depth of a display volume to be represented by a 3D ultrasound image is adjusted, a position of a surface of the display volume on a 2D ultrasound image, according to an embodiment.

FIG. 4 is a flowchart of a method, performed by the ultrasound diagnosis apparatus 1000, of displaying, as a depth of a display volume to be represented by a 3D ultrasound image is adjusted, a position of a surface of the display volume on a 2D ultrasound image, according to an embodiment.

The ultrasound diagnosis apparatus 1000 may display a 2D ultrasound image of an object and a 3D ultrasound image thereof showing an ROI set in the 2D ultrasound image (S410). The ultrasound diagnosis apparatus 1000 may determine points in the 2D ultrasound image corresponding to a surface of a display volume of the object represented by the 3D ultrasound image (S420). The ultrasound diagnosis apparatus 1000 may display the determined points on the 2D ultrasound image (S430). Operations S410, S420, and S430 may be described with reference to operations S210, S220, and S230 described with reference to FIG. 2.

The ultrasound diagnosis apparatus 1000 may receive a user input for adjusting a depth of the surface of the display volume (S440).

The user input for adjusting a depth of the surface of the display volume may include a user input for adjusting a range of opacity of a pixel to be rendered as a 3D ultrasound image during volume rendering. According to an embodiment, parameters for adjusting a range of opacity of a pixel to be rendered as a 3D ultrasound image may be referred to as "threshold.low" and "threshold.high". For example, if a user input for setting parameters "threshold.low" and "threshold.high" respectively to a first value and a second value is received, the ultrasound diagnosis apparatus 1000 may render only voxels having the first or second value within a range of opacities from 0 to 255 as a 3D ultrasound image.

Furthermore, the user input for adjusting a depth of the surface of the display volume may include an input for performing a function of removing a part of the display volume. For example, the ultrasound diagnosis apparatus 1000 may provide an automatic face detection function for automatically removing a display volume covering a fetal face so that the fetal face may be clearly seen on a 3D ultrasound image. When a user input for performing an automatic face detection function is received, the ultrasound diagnosis apparatus 1000 may remove a display volume (e.g., the placenta or hand) covering a fetal face.

Furthermore, for example, if a region in the 3D ultrasound image is touched, or a cursor is located thereon, the ultrasound diagnosis apparatus 1000 may provide a function of removing a display volume corresponding to the touched region or the region where the cursor is located in such a way as to melt away the display volume. Furthermore, when a user input for selecting a region from the 3D ultrasound image is received, the ultrasound diagnosis apparatus 1000 may provide a function of cutting out a display volume corresponding to the selected region. For example, if a user input for selecting a fetal hand covering a fetal face from the 3D ultrasound image is received, the ultrasound diagnosis apparatus 1000 may cut out a display volume corresponding to the fetal hand.

Furthermore, the user input for adjusting a depth of the surface of the display volume may include a user input for performing a function of automatically removing noise data from 3D data.

After the depth of the surface of the display volume has been adjusted, the ultrasound diagnosis apparatus 1000 may change a depth of the points displayed on the 2D ultrasound image (S450).

For example, after the depth of the surface of the display volume has been changed, the ultrasound diagnosis apparatus 1000 may change a depth of points in the 2D ultrasound image corresponding to the surface of the display volume. For example, when the display volume is deleted from the 3D ultrasound image, the ultrasound diagnosis apparatus 1000 may move down a position of the points in the 2D ultrasound image corresponding to the surface of the display volume.

Figure 5:
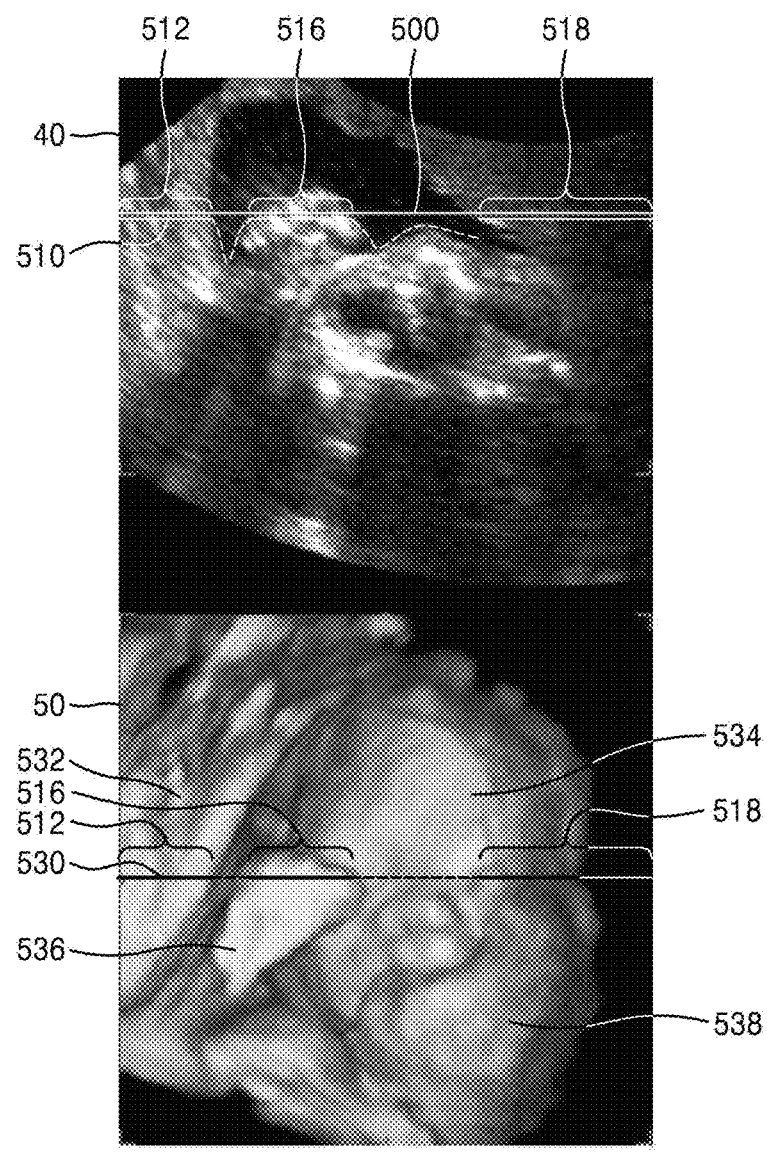
FIG. 5 illustrates an example in which an ultrasound diagnosis apparatus displays, on a 3D ultrasound image, a line representing a position of a cross-section of an object shown in a 2D ultrasound image, according to an embodiment.

FIG. 5 illustrates an example in which the ultrasound diagnosis apparatus 1000 displays, on a 3D ultrasound image, a line representing a position of a cross-section of an object shown in a 2D ultrasound image, according to an embodiment.

Referring to FIG. 5, the ultrasound diagnosis apparatus 1000 may display points having the same depth as a depth of starting points, i. e., points 500 where 3D rendering will start, and that are selected by the user, from among points 510 in a 2D ultrasound image 40 corresponding to a surface of a display volume, in such a manner that the points having the same depth as the depth of the points 500 are distinguished from points having depths different from that same depth.

The ultrasound diagnosis apparatus 1000 may display the 2D ultrasound image 40 showing a cross-section of a pregnant woman's uterus. In the 2D ultrasound image 40, a uterine wall, a fetus, and a placenta may appear bright while an amniotic fluid may appear dark.

Furthermore, the ultrasound diagnosis apparatus 1000 may receive a user input for selecting the points 500 where 3D rendering will start. The user input for selecting the points 500 may mean a user input for selecting a depth of starting points where 3D rendering will start.

The ultrasound diagnosis apparatus 1000 may display a 3D ultrasound image 50 based on the selected points 500. The 3D ultrasound image 50 may show a uterine wall 532, a fetus 534, a hand 536, and a placenta 538. Furthermore, the ultrasound diagnosis apparatus 1000 may display a position of the surface of the display volume represented by the 3D ultrasound image 50 on the 2D ultrasound image 40 as a line connecting the points 510.

The ultrasound diagnosis apparatus 1000 may display points rendered as the surface of the display volume from among the points 500 selected as a position where 3D rendering will start in such a manner that the points are distinguished from points not rendered as the surface of the display volume.

For example, from among the points 500 in the 2D ultrasound image 40 selected as a position where the 3D rendering will start, points 512 passing over the uterine wall, points 514 passing over the fetal hand, or points 518 passing over the placenta may be rendered as the surface of the display volume while the remaining points passing over the amniotic fluid may not be rendered as the surface of the display volume.

Thus, the ultrasound diagnosis apparatus 1000 may display as a solid line points corresponding to the points 512, 516, or 518 respectively passing over the uterine wall, the fetal hand, or the placenta from among the points 510 representing the position of the surface of the display volume, while displaying points corresponding to the remaining points passing over the amniotic fluid as a dashed line.

Furthermore, although not shown in FIG. 5, the ultrasound diagnosis apparatus 1000 may display as a solid line the points 512, 516, or 518 respectively passing over the uterine wall, the fetal hand, or the placenta from among the points 500 selected as a position where 3D rendering will start, while displaying the remaining points passing over the amniotic fluid as a dashed line.

The ultrasound diagnosis apparatus 1000 may display, on the 3D ultrasound image 50, a position of a cross-section of the object represented by the 2D ultrasound image 40 as a line connecting points 530.

Furthermore, referring to FIG. 5, the ultrasound diagnosis apparatus 1000 may display points, each point being where the surface of the display volume has the same depth as a depth of starting points, i.e., the points 500 where 3D rendering will start, and that are selected by the user, from among the points 530 in the 3D ultrasound image 50 corresponding to the cross-section of the object represented by the 2D ultrasound image 40, in such a manner that the points are distinguished from points where the surface of the display volume has different depths than the depth of the points 500.

For example, a depth of the surface of the display volume represented at each of the points 512 passing over the uterine wall, the points 516 passing over the fetal hand, or the points 518 passing over the placenta, from among the points 530 representing the position of the cross-section of the object in the 3D ultrasound image 50, is equal to a depth of the points 500 where 3D rendering will start and being selected from the 2D ultrasound image 40. However, since the remaining ones of the points 530 correspond to some of the points 500 representing the amniotic fluid, a depth of the surface of the display volume represented at the remaining points is greater than the depth of the points 500.

Thus, the ultrasound diagnosis apparatus 1000 may display as a solid line the points corresponding to the points 512, 516, or 518 respectively passing over the uterine wall, the fetal hand, or the placenta from among the points 530 representing the position of the cross-section of the object, while displaying the remaining points as a dashed line.

Figure 6A:
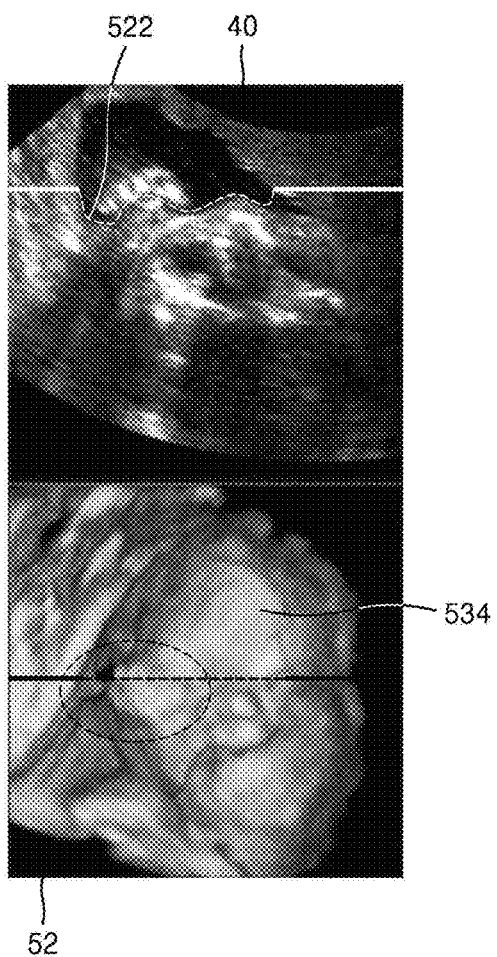
FIGS. 6A through 6C illustrate examples in which an ultrasound diagnosis apparatus displays, when a depth of a surface of a display volume represented by 3D ultrasound images is adjusted, a position of the surface of the display volume on a 2D ultrasound image, according to an embodiment.
Figure 6B:
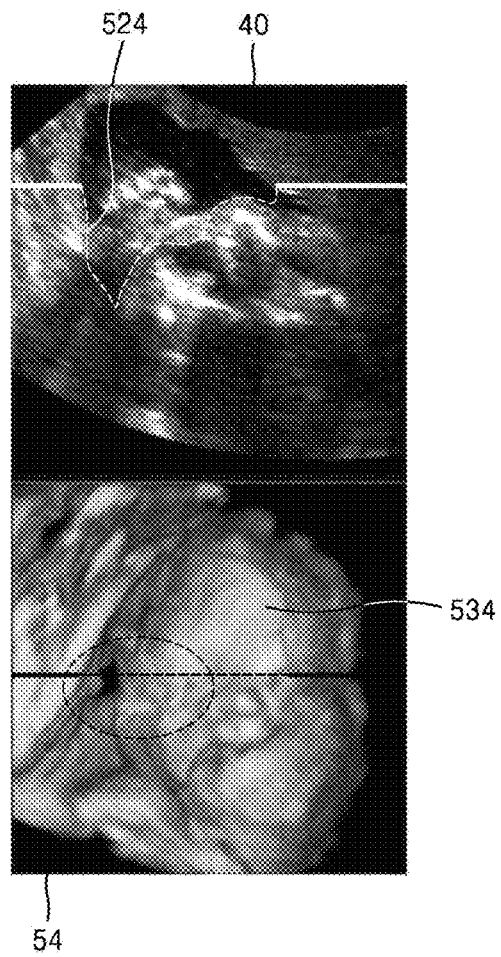
Figure 6C:
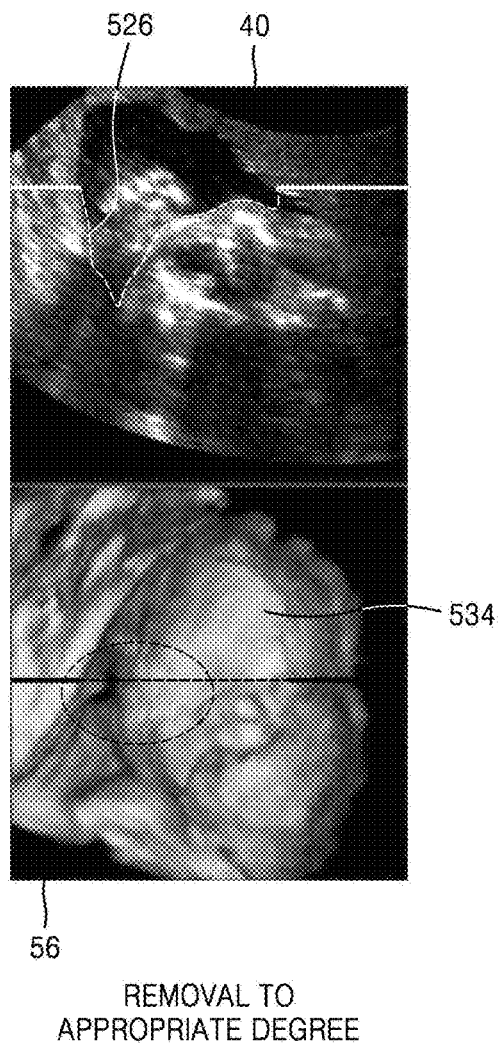

FIGS. 6A through 6C illustrate examples in which the ultrasound diagnosis apparatus 1000 displays, as a depth of a display volume shown in 3D ultrasound images is adjusted, a position of a surface of the display volume on 2D ultrasound images, according to an embodiment.

Referring to FIGS. 6A through 6C, the ultrasound diagnosis apparatus 1000 may display adjusted positions of surfaces of display volumes on 2D ultrasound images 40.

Referring back to FIG. 5, the fetus 534 displayed on the 3D ultrasound image 50 may cover his or her eye with the hand 536. To represent a face of the fetus 534 with the hand 536 removed therefrom as a display volume, the user may cut out the hand 536 of the fetus 534 by adjusting a 3D rendering parameter with respect to the hand 536.

The 2D ultrasound images 40 shown in FIGS. 6A through 6C correspond to the 2D ultrasound image 40 described with reference to FIG. 5, and 3D ultrasound images 52, 54, and 56 shown in FIGS. 6A through 6C may be images showing surfaces of the display volumes modified according to the degree to which the hand 536 has been cut out from the 3D ultrasound image 50 shown in FIG. 5

FIG. 6A shows an example in which the hand 536 of the fetus 534 has been removed to a lesser degree than appropriate, FIG. 6B shows an example in which the hand 536 of the fetus 534 and the eye covered with the hand 534 have been removed together, and FIG. 6C shows an example in which the hand 536 of the fetus 534 has been removed to an appropriate degree.

Referring to FIG. 6A, the 3D ultrasound image 52 in which the hand 536 of the fetus 534 has been removed to a lesser degree than appropriate may represent a display volume including the face of the fetus 534 with the insufficiently removed hand 536 attached thereto. Referring to FIG. 6B, the 3D ultrasound image 54 in which even the eye of the fetus 534 as well as the hand 536 has been removed may represent a display volume with a part of the eye of the fetus 534 removed therefrom. Referring to FIG. 6C, the 3D ultrasound image 56 in which the hand 536 of the fetus 534 has been removed appropriately may represent a display volume showing a face of the fetus 534.

As a depth of the display volume in the 3D ultrasound image 50 changes, the ultrasound diagnosis apparatus 1000 may change a position of the surface of the display volume displayed on the 2D ultrasound images 40. As shown in FIGS. 6A through 6C, as the degree to which the hand 536 of the fetus 534 has been removed increases, the ultrasound diagnosis apparatus 1000 may move further down a position of points corresponding to the surface of the display volume.

By comparing positions of lines 522, 524, and 526 displayed on the 2D ultrasound images 40, each line representing a surface of the display volume, it can be seen that the line 526 shown in FIG. 6C when the hand 536 of the fetus 534 has been removed appropriately may be cut deeper than the line 522 shown in FIG. 6A when the hand 536 has been removed insufficiently. Furthermore, the line 526 may be cut shallower than the line 524 shown in FIG. 6B when even the eye of the fetus 534 has been removed.

The user may delete or restore a part of the display volume by identifying positions of points in a 2D ultrasound image corresponding to a surface of a display volume.

Figure 7:
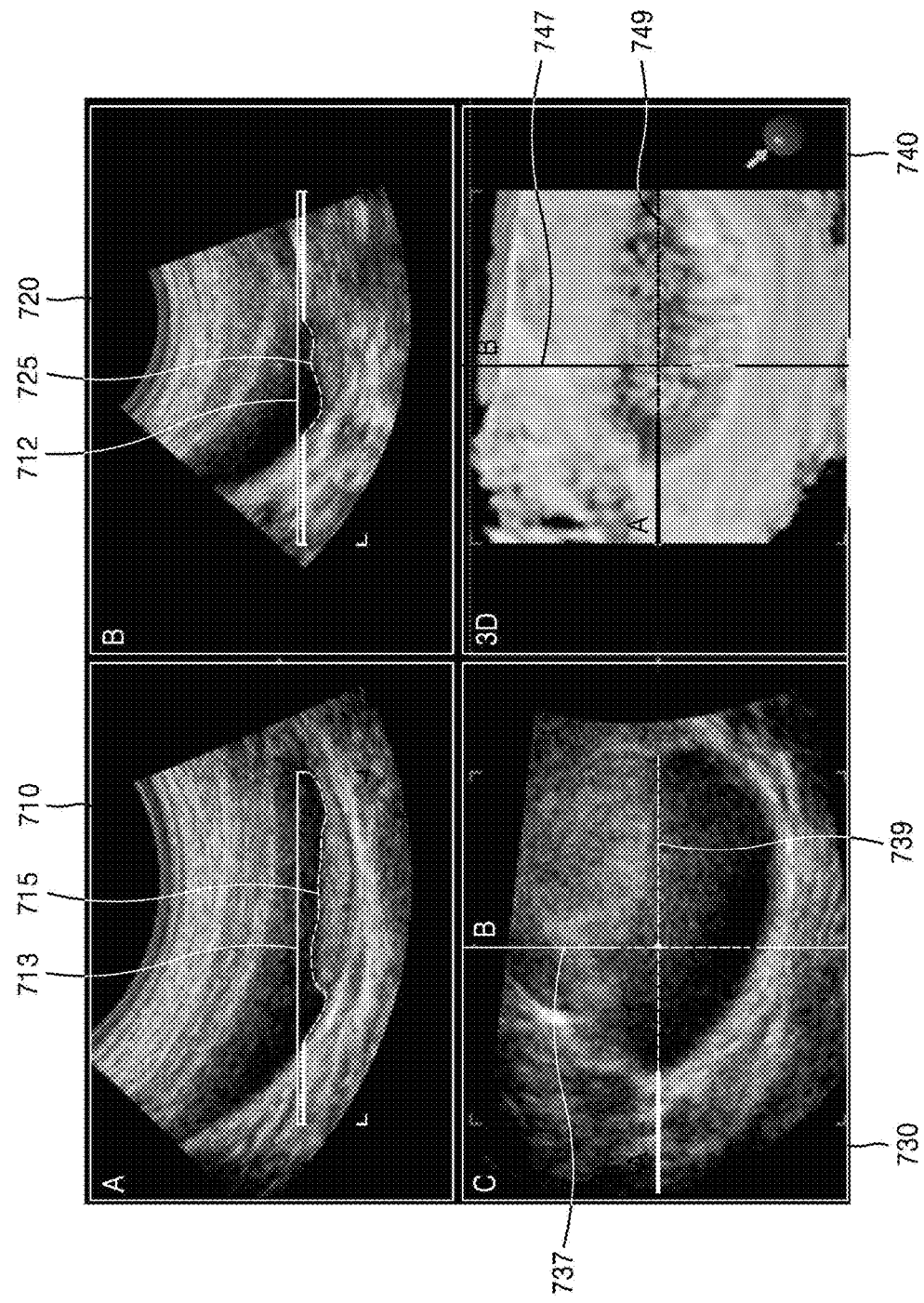
FIG. 7 illustrates an example in which an ultrasound diagnosis apparatus displays a position of a surface of a display volume represented by a 3D ultrasound image on 2D ultrasound images representing planes in different directions, according to an embodiment.

FIG. 7 illustrates an example in which the ultrasound diagnosis apparatus 1000 displays a position of a surface of a display volume represented by a 3D ultrasound image on 2D ultrasound images respectively representing planes in different directions, according to an embodiment.

Referring to FIG. 7, the ultrasound diagnosis apparatus 1000 may display a position of a surface of a display volume represented by a 3D ultrasound image 740 on 2D ultrasound images 710, 720, and 730 respectively representing planes in different directions.

The ultrasound diagnosis apparatus 1000 may display the 2D ultrasound image 710 representing a sagittal plane or A plane together with the 2D ultrasound image representing a coronal plane or B plane. Furthermore, the ultrasound diagnosis apparatus 1000 may display the 3D ultrasound image 740 with respect to an ROI 713 set in the 2D ultrasound image 710 in the sagittal plane and an ROI 723 set in the 2D ultrasound image 720 in the coronal plane, together with the 2D ultrasound images 710 and 720 in the sagittal plane and the coronal plane. Furthermore, the ultrasound diagnosis apparatus 1000 may display the 2D ultrasound image 730 representing an axial plane or C plane. The axial plane or C plane may be in the same direction as a view plane of the 3D ultrasound image 740.

The ultrasound diagnosis apparatus 1000 may display, on the 3D ultrasound image 740, positions of cross-sections of an object represented by the 2D ultrasound images 710 and 720. For example, the ultrasound diagnosis apparatus 1000 may display on the 3D ultrasound image 740 markers 749 and 747 respectively indicating the positions of the cross-sections of the object represented by the 2D ultrasound images 710 and 720 in the sagittal plane and the coronal plane.

Furthermore, the ultrasound diagnosis apparatus 1000 may display on the 2D ultrasound image 730 in the axial plane markers 739 and 737 respectively indicating the positions of the cross-sections of the object represented by the 2D ultrasound images 710 and 720 in the sagittal plane and the coronal plane.

The ultrasound diagnosis apparatus 1000 may display a position of a surface of the display volume represented by the 3D ultrasound image 740 on the 2D ultrasound images 710 and 720. For example, the ultrasound diagnosis apparatus 1000 may display a marker 715 indicating a position of the surface of the display volume on the 2D ultrasound image 710 in the sagittal plane. Furthermore, the ultrasound diagnosis apparatus 1000 may display a marker 725 indicating a position of the surface of the display volume on the 2D ultrasound image 720 in the coronal plane.

In this case, the ultrasound diagnosis apparatus 1000 may display the markers 715, 725, 747, and 749 so that the marker 749 indicating the position of the sagittal plane and displayed on the 3D ultrasound image 740 may correspond to the marker 715 indicating the position of the surface of the display volume and displayed on the 2D ultrasound image 710 in the sagittal plane and that the marker 747 indicating the position of the coronal plane and displayed on the 3D ultrasound image 740 may correspond to the marker 725 indicating the position of the surface of the display volume and displayed on the 2D ultrasound image 720 in the coronal plane. For example, the ultrasound diagnosis apparatus 1000 may display the markers 715 and 749 related to the sagittal plane in a red color while displaying the markers 725 and 747 related to the coronal plane in a green color.

Figure 8A:
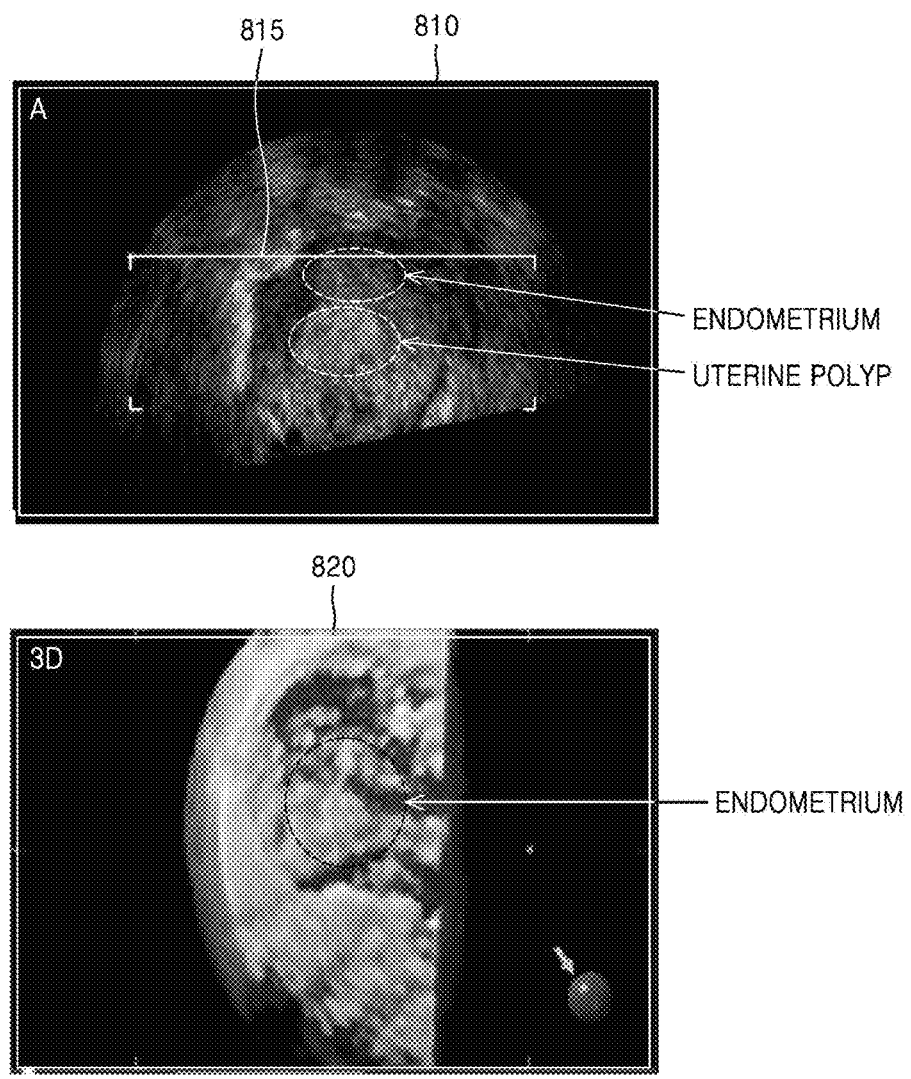
FIGS. 8A and 8B illustrate an example in which an ultrasound diagnosis apparatus displays, when a depth of a display volume represented by a 3D ultrasound image is adjusted, a position of a surface of the display volume on a 2D ultrasound image, according to another embodiment.
Figure 8B:
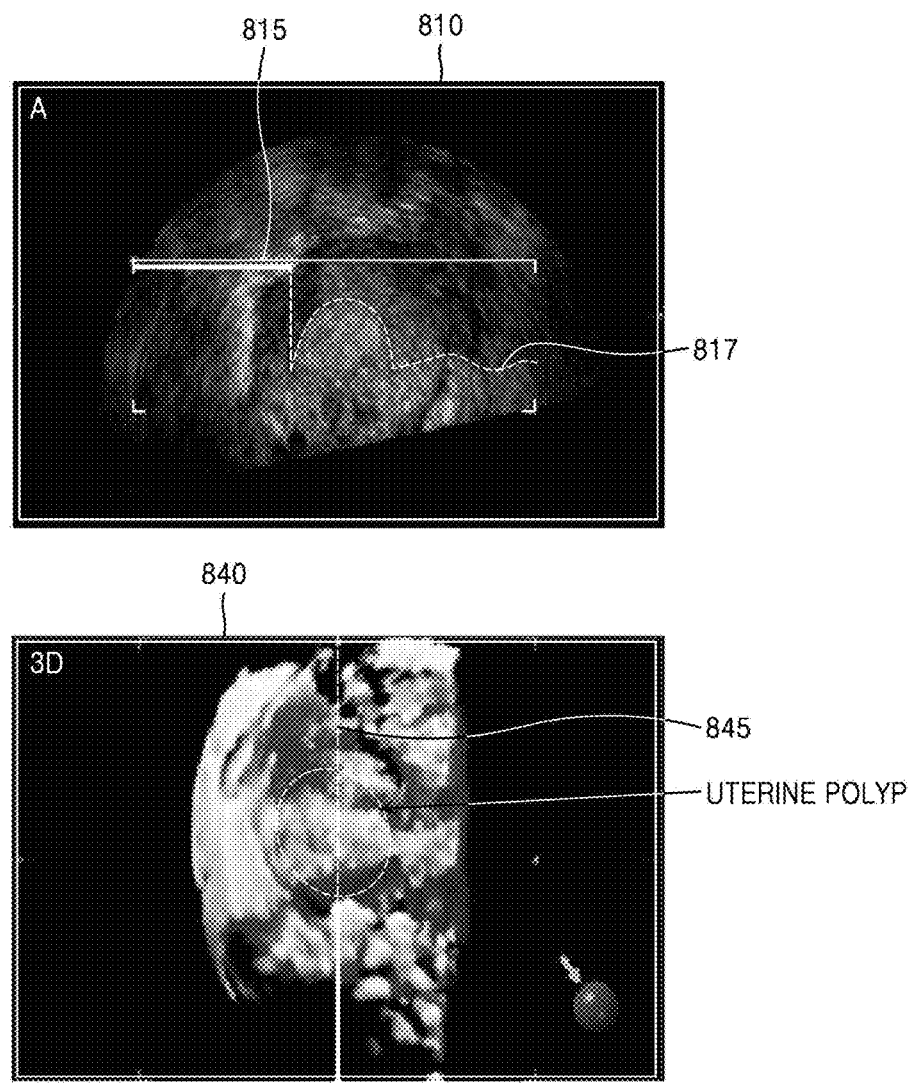

FIGS. 8A and 8B illustrate an example in which the ultrasound diagnosis apparatus 1000 displays, as a depth of a display volume shown in a 3D ultrasound image is adjusted, a position of a surface of the display volume on a 2D ultrasound image, according to another embodiment.

Referring to FIG. 8A, the ultrasound diagnosis apparatus 1000 may display a 2D ultrasound image 810 showing a uterus where a polyp occurs. The 2D ultrasound image 810 may show an endometrium and a polyp located below the endometrium.

When a user input for setting an ROI 815 in the 2D ultrasound image 810 is received, the ultrasound diagnosis apparatus 1000 may display a 3D ultrasound image 820 with respect to the set ROI 815. The 3D ultrasound image 820 may show a display volume representing the endometrium as a surface. To examine the polyp located below the endometrium, the user may cut out the endometrium by using a user interface included in the ultrasound diagnosis apparatus 1000.

Referring to FIG. 8B, when a user input for cutting out the endometrium shown in the 3D ultrasound image 820 is received, the ultrasound diagnosis apparatus 1000 may remove the endometrium and display a 3D ultrasound image 840 representing a polyp in the endometrium as a surface of a display volume.

Furthermore, the ultrasound diagnosis apparatus 1000 may display on the 2D ultrasound image 810 a marker 817 indicating a position of a surface of a uterine polyp displayed on the 3D ultrasound image 840. Furthermore, the ultrasound diagnosis apparatus 1000 may display a position 845 of a cross-section of an object represented by the 2D ultrasound image 810.

FIG. 9 illustrates an example in which the ultrasound diagnosis apparatus 1000 displays on a 2D ultrasound image a position of a surface of a display volume represented by an ultrasound virtual endoscopic image, according to an embodiment.

Referring to FIG. 9, the ultrasound diagnosis apparatus 1000 may display on a 2D ultrasound image 910 a position of a surface of a display volume represented by a 3D ultrasound virtual endoscopic image 920.

The ultrasound diagnosis apparatus 1000 may display the 2D ultrasound image 910 of a patient's blood vessel and the 3D ultrasound virtual endoscopic image 920 generated based on the 2D ultrasound image 910 of the patient's blood vessel.

For example, the ultrasound diagnosis apparatus 1000 may generate the 3D ultrasound virtual endoscopic image 920 from the 2D ultrasound image 910 by using a 3D ultrasound graphic imaging technology. The 3D ultrasound graphic imaging technology may include a prospective projection technique but is not limited thereto. According to an embodiment, a 3D ultrasound virtual endoscopy method may be referred to as a 3D ultrasound virtual simulation method. By providing the 3D ultrasound virtual endoscopic image 920, the ultrasound diagnosis apparatus 1000 may provide an image similar to that obtained using an endoscope actually inserted into the artery.

The ultrasound diagnosis apparatus 1000 may display, on the 2D ultrasound image 910, a marker 902 indicating a position of a virtual camera, a marker 904 indicating a viewing direction of the virtual camera or a direction in which the virtual camera moves, a marker 906 indicating a region being displayed on the 3D ultrasound virtual endoscopic image 920, a line 908 representing a surface depicted in the 3D ultrasound virtual endoscopic image 920, and a line 909 representing a surface not depicted in the 3D ultrasound virtual endoscopic image 920.

The ultrasound diagnosis apparatus 1000 may determine at least one point in the 2D ultrasound image 910. For example, the ultrasound diagnosis apparatus 1000 may receive a user input for selecting at least one point 912, 914, 916, and 918 on a surface of an artery 901.

After the at least one point has been determined, the ultrasound diagnosis apparatus 1000 may determine a point in the 3D ultrasound virtual endoscopic image 920 corresponding to the determined point in the 2D ultrasound image 910.

For example, the ultrasound diagnosis apparatus 1000 may determine first through fourth points 912, 914, 916, and 918 on the surface of the artery 901 as respectively corresponding to first through fourth points 922, 924, 926, and 928 in the 3D ultrasound virtual endoscopic image 920.

The ultrasound diagnosis apparatus 1000 may display, on a point in the 3D ultrasound virtual endoscopic image 920 corresponding to a point in the 2D ultrasound image 910, a marker indicating correspondence between the points.

Furthermore, the ultrasound diagnosis apparatus 1000 may display positions of points that are the same distance away from the position 902 of the virtual camera. For example, the ultrasound diagnosis apparatus 1000 may display lines 934, 936, and 938, each of which connects points that are the same distance away from the position 902 of the virtual camera, on the 3D ultrasound virtual endoscopic image 920.

Furthermore, the ultrasound diagnosis apparatus 1000 may receive a user input for selecting a point from the 3D ultrasound virtual endoscopic image 920 and display a position of a point in the 2D ultrasound image 910 corresponding to the selected point on the 2D ultrasound image 910.

Thus, when the user desires to examine a portion of interest identified in the 2D ultrasound image 910 via the 3D ultrasound virtual endoscopic image 920, the user may easily adjust a position of a viewpoint for the virtual camera and a viewing direction of the virtual camera.

Figure 10:
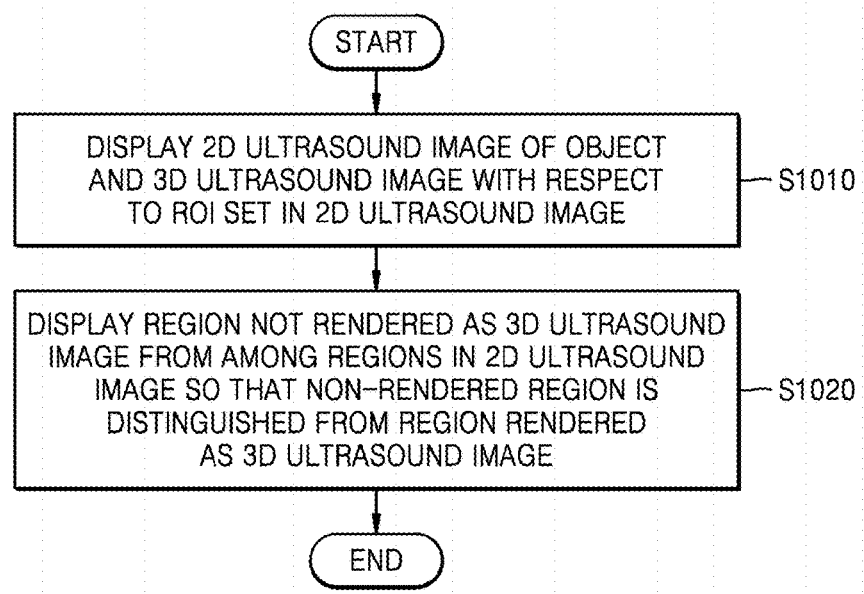
FIG. 10 is a flowchart of a method, performed by an ultrasound diagnosis apparatus 1000, of displaying, on a 2D ultrasound image, a region not rendered as a 3D ultrasound image from among regions in the 2D ultrasound image, according to an embodiment.

FIG. 10 is a flowchart of a method, performed by the ultrasound diagnosis apparatus 1000, of displaying on a 2D ultrasound image a region not rendered as a 3D ultrasound image from among regions in the 2D ultrasound image, according to an embodiment.

The ultrasound diagnosis apparatus 1000 may display a 2D ultrasound image of an object and a 3D ultrasound image thereof showing an ROI set in the 2D ultrasound image (S1010).

Operation S1010 may be described with reference to operation S210 described with reference to FIG. 2.

The ultrasound diagnosis apparatus 1000 may display a region not rendered as the 3D ultrasound image from among regions in the 2D ultrasound image in such a manner that the region is distinguished from a region rendered as the 3D ultrasound image (S1020).

For example, by displaying points in the 2D ultrasound image corresponding to a surface of a display volume represented by the 3D ultrasound image, the ultrasound diagnosis apparatus 1000 may display a region rendered as the 3D ultrasound image in such a manner as to be distinguished from a region not rendered as the 3D ultrasound image. In this case, the points in the 2D ultrasound image corresponding to the surface of the display volume may be points where volume rendering starts.

Furthermore, for example, the ultrasound diagnosis apparatus 1000 may determine points in the 2D ultrasound image where volume rendering starts and then a line connecting the determined points. The ultrasound diagnosis apparatus 1000 may determine, based on a line connecting points where volume rendering starts, a region in a rendering direction from among regions in the 2D ultrasound image as being a rendered region and a region in a direction opposite to the rendering direction as being a non-rendered region.

According to an embodiment, when the 3D ultrasound image shows only a contour of a structure within a display volume and represents the inside of the structure as being transparent or semi-transparent, the ultrasound diagnosis apparatus 1000 may determine a region representing the contour of the structure from among regions in the 2D ultrasound image as being a rendered region and the inside of the structure as being a non-rendered region.

After a region not rendered as the 3D ultrasound image has been determined, the ultrasound diagnosis apparatus 1000 may display a region not rendered as the 3D ultrasound image from among regions in the 2D ultrasound image in such a manner that the region is distinguished from a region rendered as the 3D ultrasound image.

For example, the ultrasound diagnosis apparatus 1000 may display, on the 2D ultrasound image, a rendered region and a non-rendered region as a dot, a line, a plane, a geometrical shape, a color, transparency, a text, or a combination of at least two thereof.

Figure 11:
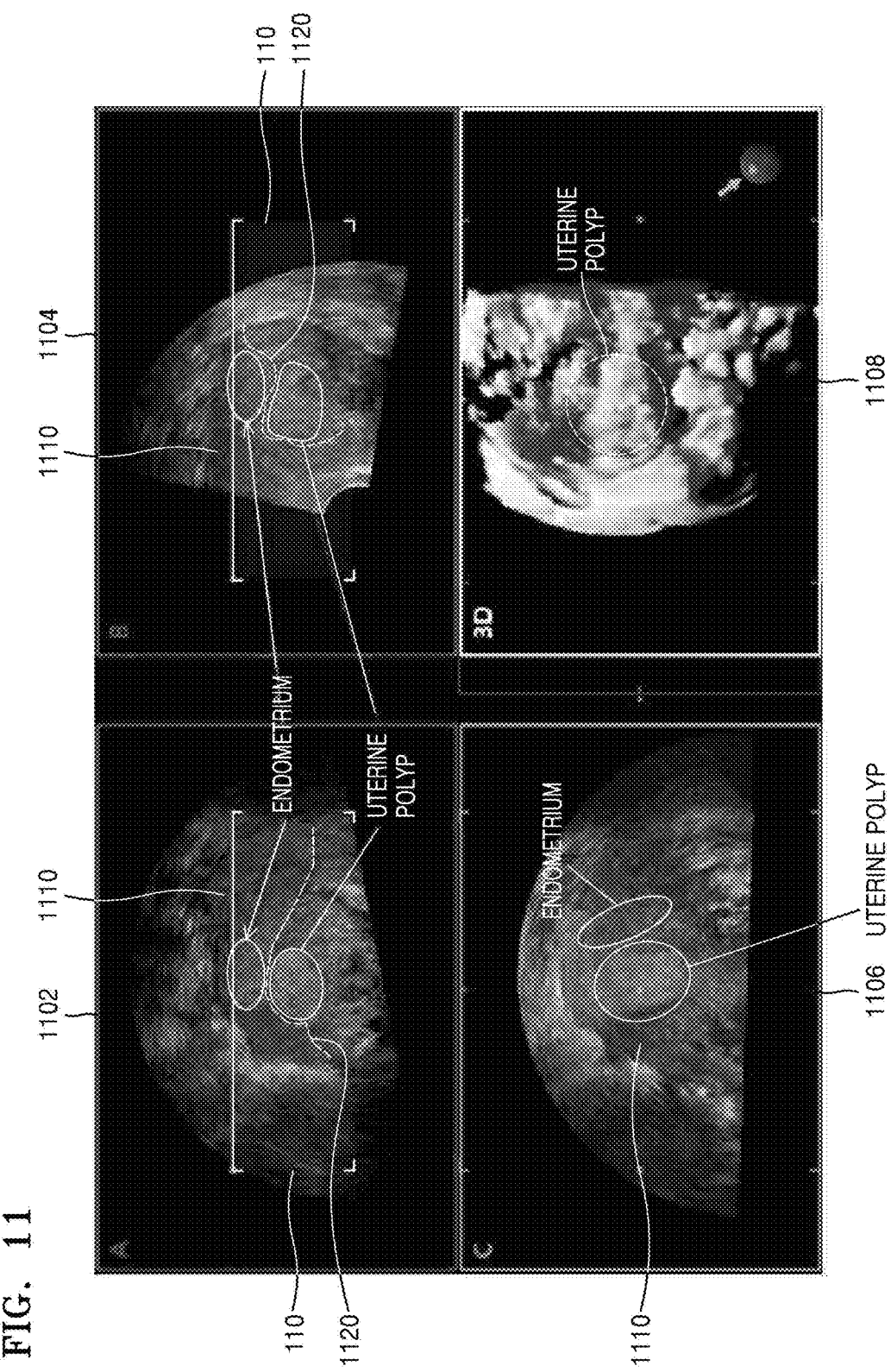
FIG. 11 illustrates an example in which an ultrasound diagnosis apparatus displays, on a 2D ultrasound image, a region not rendered as a 3D ultrasound image from among regions in the 2D ultrasound image, according to an embodiment.

FIG. 11 illustrates an example in which the ultrasound diagnosis apparatus 1000 displays on a 2D ultrasound image a region not rendered as a 3D ultrasound image from among regions in the 2D ultrasound image, according to an embodiment.

Referring to FIG. 11, the ultrasound diagnosis apparatus 1000 may display on a 2D ultrasound image a region not rendered as a 3D ultrasound image 1108 rom among regions in the 2D ultrasound image.

The ultrasound diagnosis apparatus 1000 may receive a user input for setting an ROI 110 in a cross-sectional image A 1102. When the user input for setting the ROI 110 is received, the ultrasound diagnosis apparatus 1000 may generate a 3D volume with respect to the set ROI 110. Furthermore, the ultrasound diagnosis apparatus 1000 may generate a 3D ultrasound image by rendering the generated 3D volume and display the generated 3D ultrasound image.

When the user desires to examine a 3D ultrasound image showing a uterine polyp below an endometrium, an ROI set by the user may include the uterine polyp as well as the endometrium located close to the uterine polyp. Since a starting point of the ROI is located in the endometrium, the ultrasound diagnosis apparatus 1000 may display a 3D ultrasound image representing the endometrium as a surface of a display volume. When a user input for cutting out the endometrium from the 3D ultrasound image is received, the ultrasound diagnosis apparatus 1000 may display the 3D ultrasound image 1108 representing a uterine polyp as a surface.

The ultrasound diagnosis apparatus 1000 may display a region 1110 not rendered as the 3D ultrasound image 1108 on the cross-sectional image A 1102.

For example, the ultrasound diagnosis apparatus 1000 may determine points where rendering starts from among regions in the cross-sectional image A 1102 and display a line 1120 connecting the determined points on the cross-sectional image A 1102. The line 1120 may be a line representing a position of a surface of a display volume represented by the 3D ultrasound image 1108.

The ultrasound diagnosis apparatus 1000 may determine, based on the line 1120 connecting the points where rendering starts, a region in a direction opposite to a rendering direction from among regions in the cross-sectional image A 1102 as being a non-rendered region 1110. Furthermore, the ultrasound diagnosis apparatus 1000 may display the non-rendered region 1110 in such a manner as to be distinguished from other regions. For example, the ultrasound diagnosis apparatus 1000 may display the non-rendered region 1110 in a color that can distinguish it from the other regions in the 2D ultrasound image. In this case, by displaying the non-rendered region 1110 in a color that is transparent enough to see regions in the 2D ultrasound image through the non-rendered region 1110, the ultrasound diagnosis apparatus 1000 may indicate that the non-rendered region 1110 is non-rendered while simultaneously displaying a shape of the structure represented as a B mode image.

Furthermore, the ultrasound diagnosis apparatus 1000 may display on a cross-sectional image B 1104 a region 1110 not rendered as the 3D ultrasound image 1108. Furthermore, the ultrasound diagnosis apparatus may display on a cross-sectional image C 1106 a region 1110 not rendered as the 3D ultrasound image 1108.

Thus, the user may identify regions in the set ROI 110 rendered as or not rendered as the 3D ultrasound image 1108.

FIGS. 12A through 12C illustrate examples in which the ultrasound diagnosis apparatus 1000 displays on a 2D ultrasound image a region not rendered as a 3D ultrasound image from among regions in the 2D ultrasound image, according to another embodiment.

Referring to FIG. 12, when a user input for adjusting a depth of a surface of a display volume is received, the ultrasound diagnosis apparatus 1000 may display on a 2D ultrasound image 40 the region (1110 of FIG. 11) not rendered as the 3D ultrasound image (1108 of FIG. 11) from among regions in the 2D ultrasound image 40.

The 2D ultrasound images 40 shown in FIG. 12 correspond to the 2D ultrasound image 40 described with reference to FIG. 5, and 3D ultrasound images 52, 54, and 56 shown in FIG. 12 may be images showing surfaces of the display volumes modified according to the degree to which a hand 536 of a fetus 534 has been cut out from the 3D ultrasound image 50 shown in FIG. 5.

FIG. 12A shows an example in which the hand 536 of the fetus 534 has been removed to a lesser degree than appropriate, FIG. 12B shows an example in which the hand 536 of the fetus 534 and the eye covered with the hand 534 have been removed together, and FIG. 12C shows an example in which the hand 536 of the fetus 534 has been removed to an appropriate degree.

As a depth of a display volume in the 3D ultrasound image (50 of FIG. 5) changes, the ultrasound diagnosis apparatus 1000 may display regions not rendered as 3D ultrasound images 52, 54, and 56 on the 2D ultrasound image 40. As shown in FIGS. 12A through 12C, as a depth to which the hand 536 of the fetus 534 has been removed increases, a non-rendered region shown in the 2D ultrasound image 40 may extend further downwards.

By comparing non-rendered regions displayed on the 2D ultrasound images 40, it can be seen that a region 1230 shown in FIG. 12C when the hand 536 of the fetus 534 has been removed appropriately extends further downwards than a region 1210 shown in FIG. 12A when the hand 536 has been removed insufficiently. Furthermore, a region 1220 shown in FIG. 12B when even the eye of the fetus 534 has been removed extends further down than the region 1230.

The user may delete or restore a part of the display volume by identifying regions in the 2D ultrasound image 40 that are not rendered as the 3D ultrasound images 52, 54, and 56.

Figure 13A:
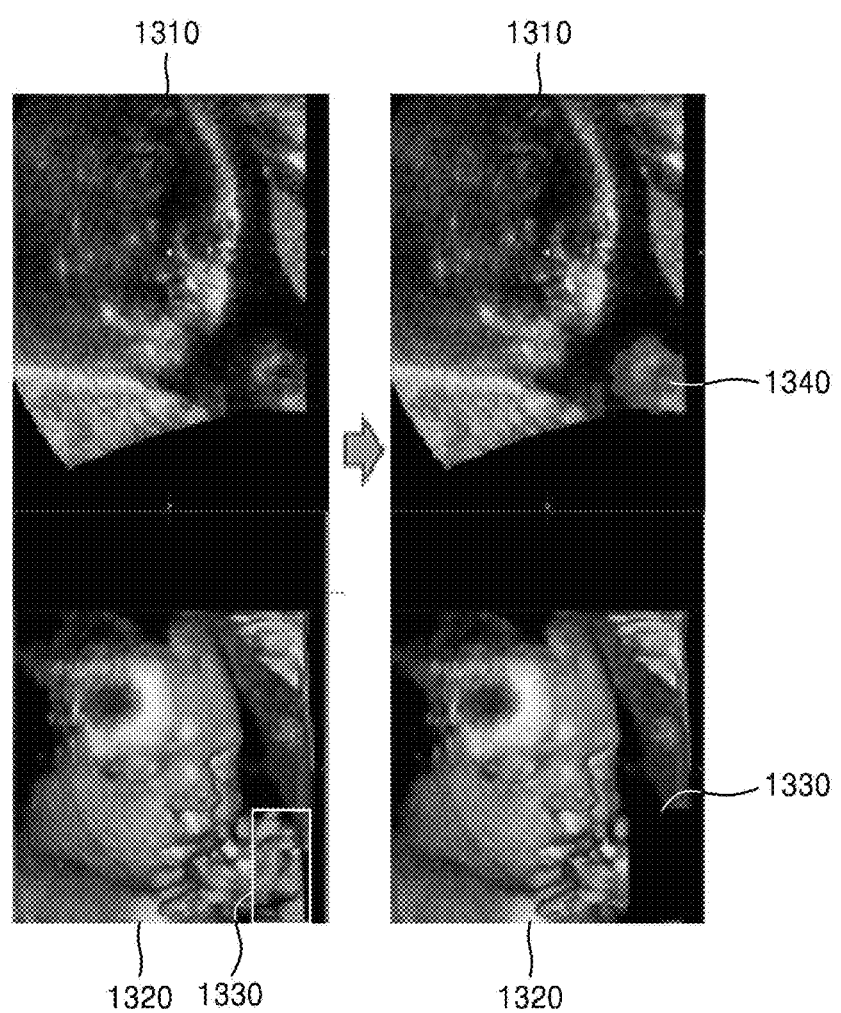
FIG. 13A illustrates an example in which an ultrasound diagnosis apparatus displays, after a region in a 3D ultrasound image has been deleted, the deleted region on a 2D ultrasound image, according to an embodiment.

FIG. 13A illustrates an example in which the ultrasound diagnosis apparatus 1000 displays, after a region in a 3D ultrasound image has been deleted, the deleted region on a 2D ultrasound image, according to an embodiment.

Referring to FIG. 13A, when a user input for deleting a region 1330 from among regions in a 3D ultrasound image 1320 is received, the ultrasound diagnosis apparatus 1000 may display a region 1340 corresponding to the deleted region 1330 on a 2D ultrasound image 1310. The region 1340 corresponding to the deleted region 1330 from among regions in the 2D ultrasound image 1310 may be a region not rendered as the 3D ultrasound image 1320.

For example, the ultrasound diagnosis apparatus 1000 may set an ROI in the 2D ultrasound image 1310 and display the 3D ultrasound image 1320 with respect to the set ROI. The 2D ultrasound image 1310 may be one of cross-sectional images that constitute a display volume represented by the 3D ultrasound image 1320. In this case, a user input for deleting the region 1330 from among regions in the 3D ultrasound image 1320 may be received.

When the user input for deleting the region 1330 from among regions in the 3D ultrasound image 1320 is received, the ultrasound diagnosis apparatus 1000 may determine the region 1340 in the 2D ultrasound image 1310 corresponding to the deleted region 1330 in the 3D ultrasound image 1320. For example, the ultrasound diagnosis apparatus 1000 may determine a volume region in a display volume corresponding to the deleted region 1330 in the 3D ultrasound image 1320 and determine a region where the determined volume region intersects a cross-section represented by the 2D ultrasound image 1310 as being the region 1340 in the 2D ultrasound image 1310 corresponding to the deleted region 1330 in the 3D ultrasound image 1320.

After determining the region 1340 in the 2D ultrasound image 1310 corresponding to the deleted region 1330 in the 3D ultrasound image 1320, the ultrasound diagnosis apparatus 1000 may indicate that the determined region 1340 corresponds to a region deleted from the 3D ultrasound image 1320 on the determined region 1340.

Figure 13B:
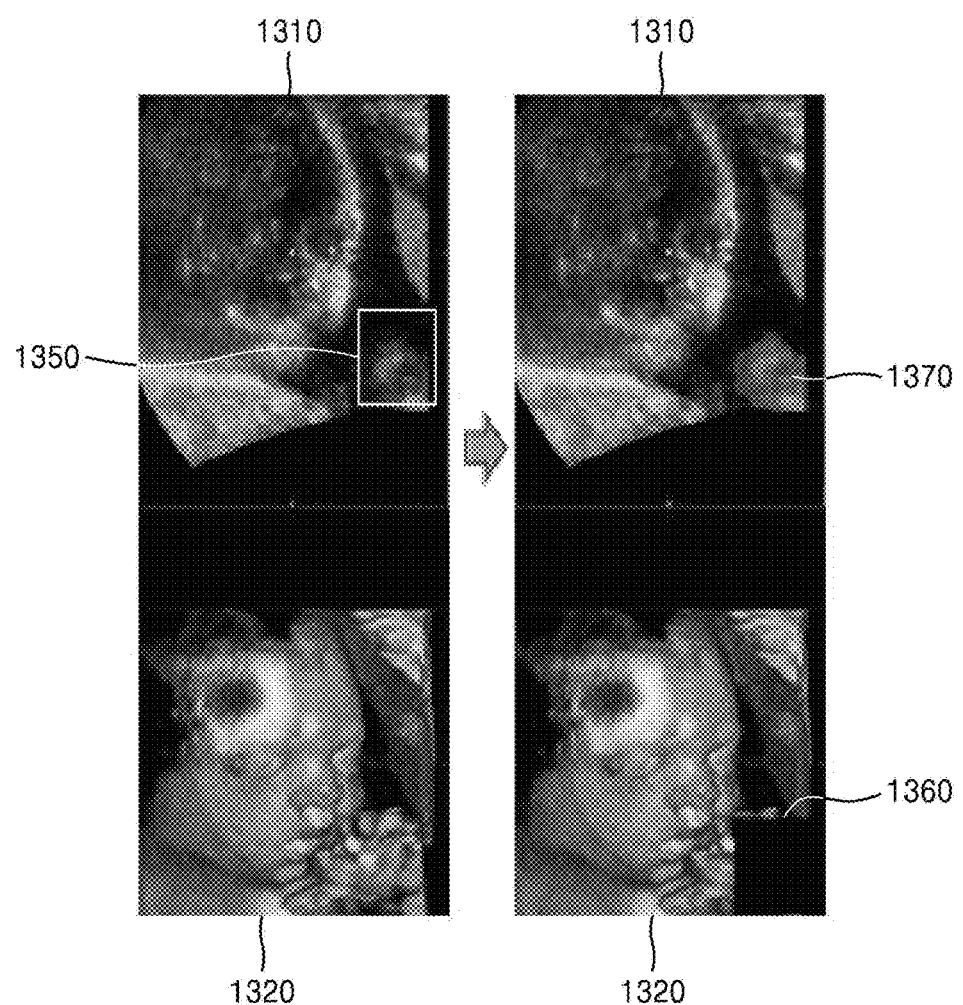
FIG. 13B illustrates an example in which an ultrasound diagnosis apparatus displays, after a region in a 2D ultrasound image has been deleted, the deleted region on a 3D ultrasound image, according to an embodiment.

FIG. 13B illustrates an example in which the ultrasound diagnosis apparatus 1000 displays, after a region in a 2D ultrasound image has been deleted, the deleted region on a 3D ultrasound image, according to an embodiment.

Referring to FIG. 13B, when a user input for deleting a region 1350 from among regions in a 2D ultrasound image 1310 is received, the ultrasound diagnosis apparatus 1000 may display a region 1360 corresponding to the deleted region 1350 on a 3D ultrasound image 1320.

When the user input for deleting the region 1350 from among regions in the 2D ultrasound image 1310 is received, the ultrasound diagnosis apparatus 1000 may determine the region 1360 in the 3D ultrasound image 1320 corresponding to the deleted region 1350 in the 2D ultrasound image 1310. For example, the ultrasound diagnosis apparatus 1000 may determine a volume region including the deleted region 1350 in the 2D ultrasound image 1310 in a display volume represented by the 3D ultrasound image 1320 and determine a region in the 3D ultrasound image 1320 represented by rendering the determined volume region as being the region 1360 in the 3D ultrasound image 1320 corresponding to the deleted region 1350 in the 2D ultrasound image 1310.

After determining the region 1360 in the 3D ultrasound image 1320 corresponding to the deleted region 1350 in the 2D ultrasound image 1310, the ultrasound diagnosis apparatus 1000 may indicate that the determined region 1360 corresponds to a region deleted from the 2D ultrasound image 1310 on the determined region 1360.

Furthermore, the ultrasound diagnosis apparatus 1000 may display a region 1370 not rendered as the 3D ultrasound image 1320 from among regions in the 2D ultrasound image 1310.

Figure 14A:
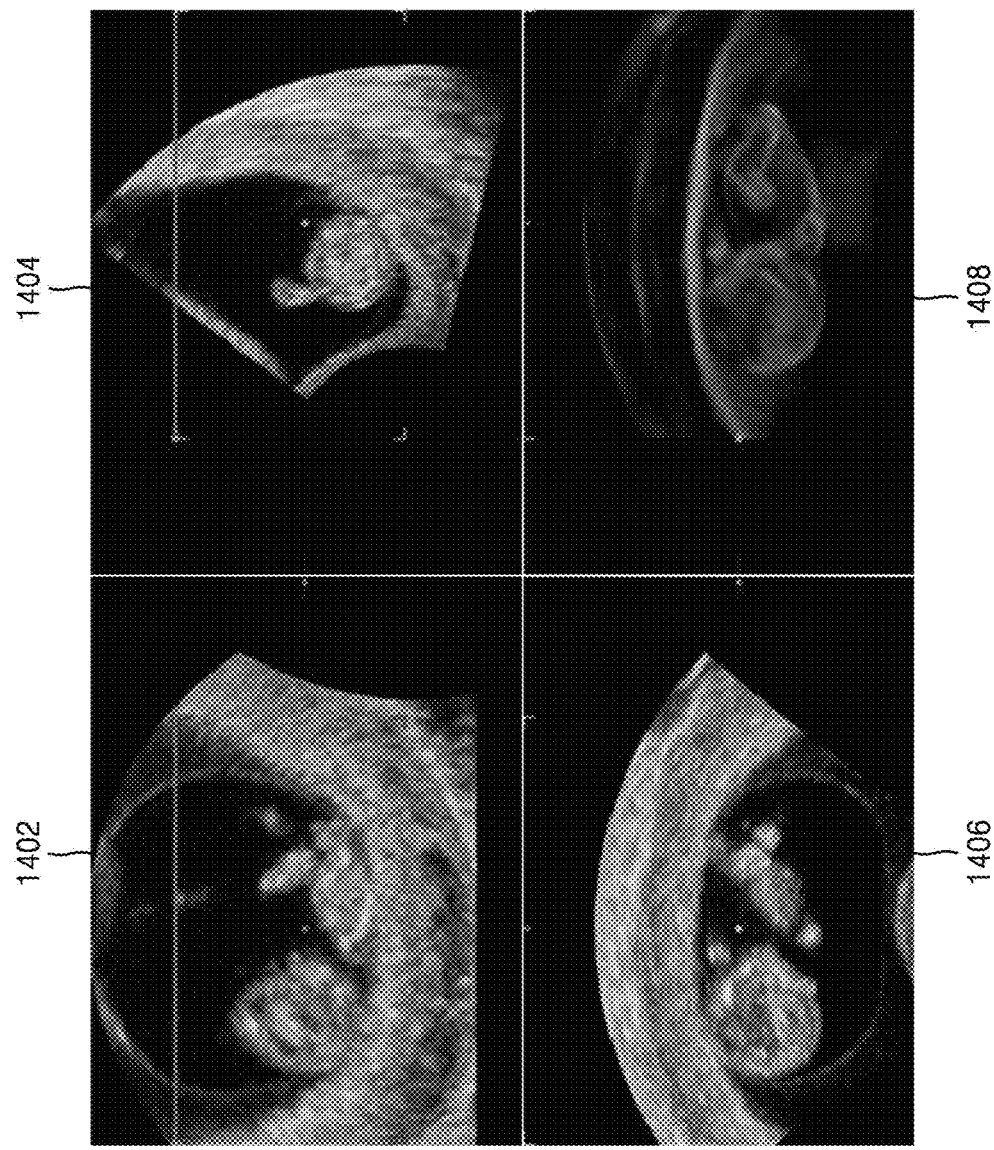
FIGS. 14A and 14B are examples in which an ultrasound diagnosis apparatus displays, on a 2D ultrasound image, a region not rendered as a 3D ultrasound image from among regions in the 2D ultrasound image, according to another embodiment.
Figure 14B:
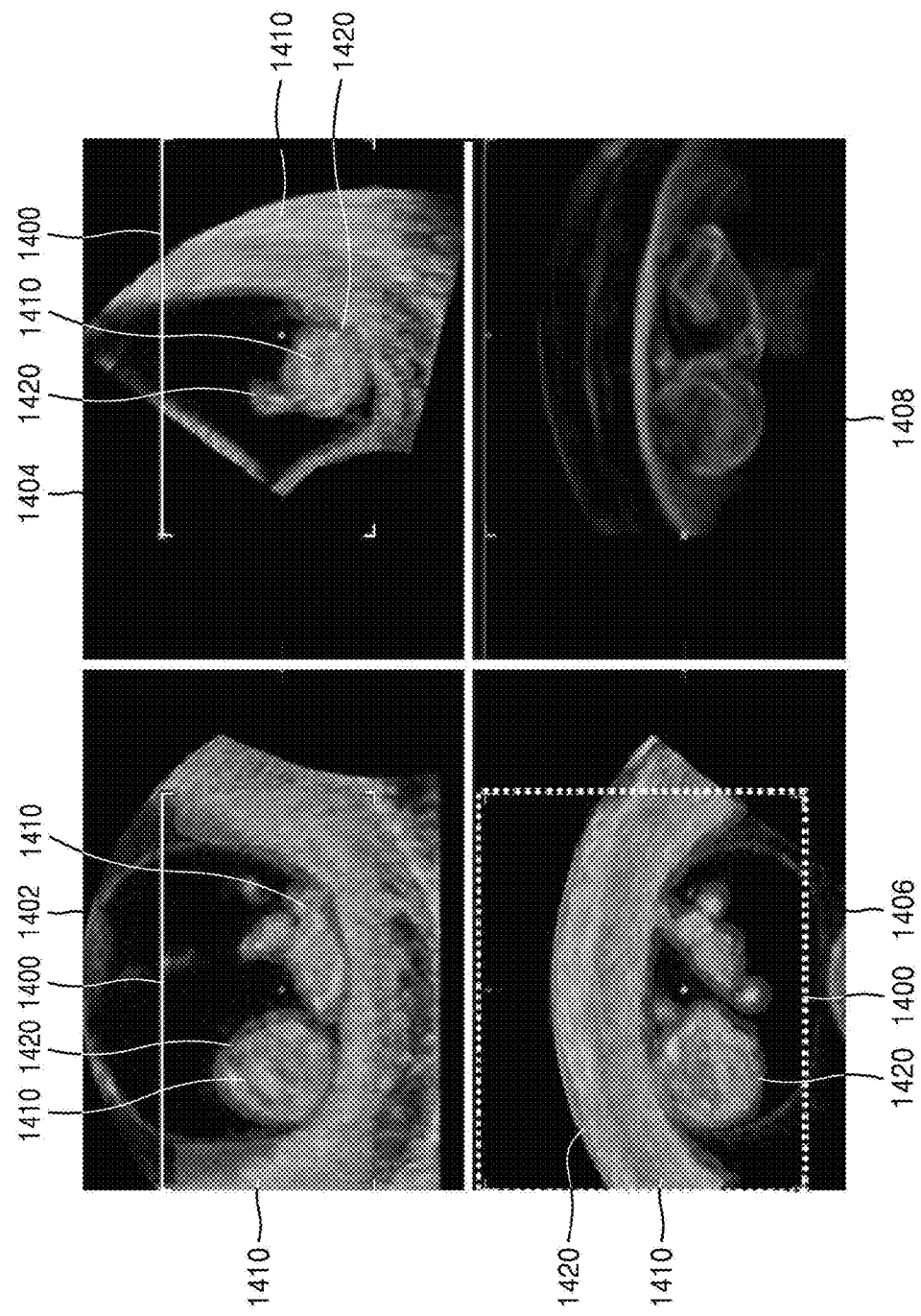

FIGS. 14A and 14B are examples in which the ultrasound diagnosis apparatus 1000 displays on a 2D ultrasound image a region not rendered as a 3D ultrasound image from among regions in the 2D ultrasound image, according to another embodiment.

Referring to FIG. 14A, the ultrasound diagnosis apparatus 1000 may display 2D ultrasound images 1402, 1404, and 1406 showing different cross-sections of a fetus inside an uterus and a 3D ultrasound image 1408 with respect to an ROI set in the 2D ultrasound image 1402.

In this case, the ultrasound diagnosis apparatus 1000 may display a 3D ultrasound image 1408 showing only a contour of a display volume with the inside thereof represented as being transparent or semi-transparent, instead of a 3D ultrasound image representing a surface of the display volume as shown in FIG. 5. For example, the ultrasound diagnosis apparatus 1000 may display the 3D ultrasound image 1408 showing only a contour of a fetus while representing the inside of the fetus as being transparent or semi-transparent.

Referring to FIG. 14B, the ultrasound diagnosis apparatus 1000 may display, on the 2D ultrasound images 1402, 1404, and 1406, regions not rendered as the 3D ultrasound image 1408 from among regions in the 2D ultrasound images 1402, 1404, and 1406.

When the 3D ultrasound image 1408 shows only a contour of a structure within the display volume, the ultrasound diagnosis apparatus 1000 may display only contours 1410 of a fetus's skin in the 2D ultrasound images 1402, 1404, and 1406 as rendered regions while displaying internal regions 1420 of the fetus as non-rendered regions.

Figure 15:
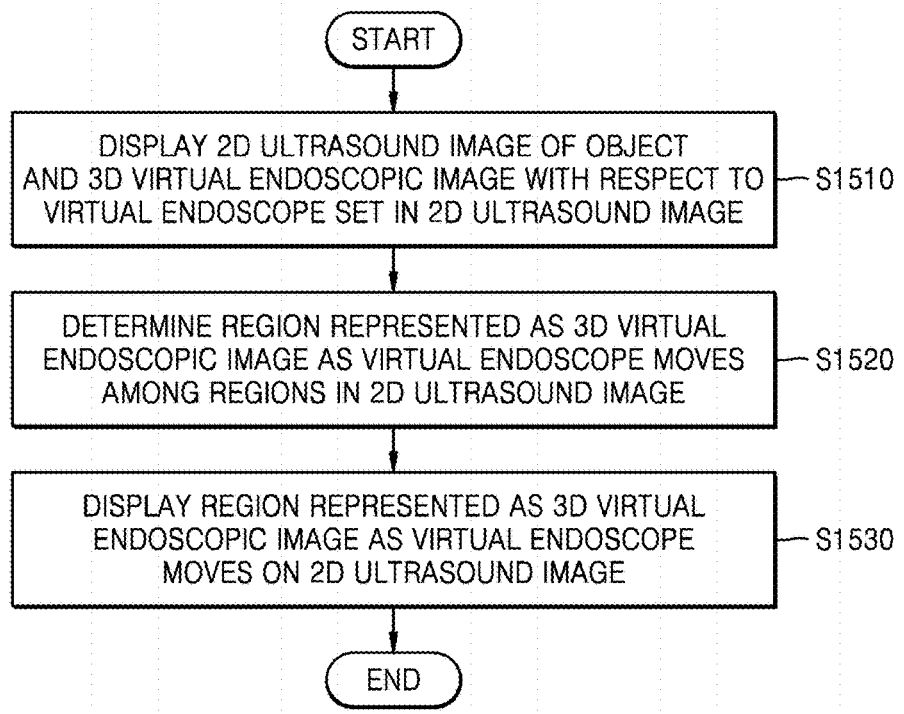
FIG. 15 is a flowchart of a method, performed by an ultrasound diagnosis apparatus, of displaying a region represented as a 3D virtual endoscopic image on a 2D ultrasound image, according to an embodiment.

FIG. 15 is a flowchart of a method, performed by the ultrasound diagnosis apparatus 1000, of displaying a region represented as a 3D virtual endoscopic image on a 2D ultrasound image, according to an embodiment.

The ultrasound diagnosis apparatus 1000 may display a 2D ultrasound image of an object and a 3D virtual endoscopic image with respect to a virtual endoscope set in the 2D ultrasound image (S1510).

The ultrasound diagnosis apparatus 1000 may determine, from among regions in the 2D ultrasound image, a region represented as the 3D virtual endoscopic image as the virtual endoscope moves (S1520).

The 2D ultrasound image may be an image showing a structure consisting of tubes such as blood vessels. When a user input for setting a camera position, a direction of camera movement, and an imaging region in the 2D ultrasound image is received, the ultrasound diagnosis apparatus 1000 may display the inside of the structure as the 3D virtual endoscopic image, based on the set camera position, direction of camera movement, and imaging region.

In this case, the ultrasound diagnosis apparatus 1000 may determine a region rendered as the 3D virtual endoscopic image as the virtual endoscope moves from among regions in the 2D ultrasound image.

The ultrasound diagnosis apparatus 1000 may display, on the 2D ultrasound image, the region rendered as the 3D virtual endoscopic image as the virtual endoscope moves (S1530).

When a user input for moving the virtual endoscope is received, the ultrasound diagnosis apparatus 1000 may display a region that has been rendered even once as the 3D virtual endoscopic image on the 2D ultrasound image in such a manner that a section that has been observed by the user even once is distinguished from a section that has never been observed by the user.

Figure 16:
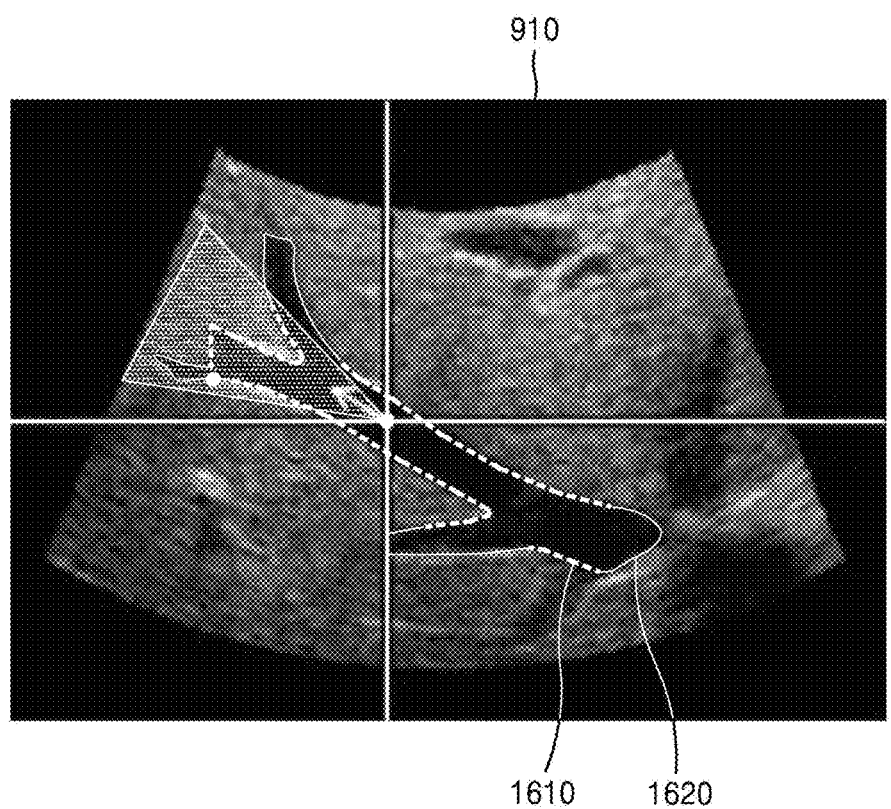
FIG. 16 illustrates an example in which an ultrasound diagnosis apparatus displays a region represented as a 3D virtual endoscopic image on a 2D ultrasound image, according to an embodiment.

FIG. 16 illustrates an example in which the ultrasound diagnosis apparatus 1000 displays a region represented as a 3D virtual endoscopic image on a 2D ultrasound image, according to an embodiment.

Referring to FIGS. 9 and 16, the ultrasound diagnosis apparatus 1000 may display a region 1610 rendered as the 3D ultrasound virtual endoscopic image 920 from among regions in the 2D ultrasound image 910 showing a blood vessel in such a manner that the region 1610 is distinguished from a region 1620 not rendered as the 3D ultrasound virtual endoscopic image 920.

For example, the ultrasound diagnosis apparatus 1000 may display as a dashed line the region 1610 that has been rendered as a 3D virtual endoscopic image even once while displaying the region 1620 that has never been rendered as the 3D virtual endoscopic image as a solid line. As another example, the ultrasound diagnosis apparatus 1000 may display the region 1610 in a yellow color and the region 1620 in a green color.

Figure 17:
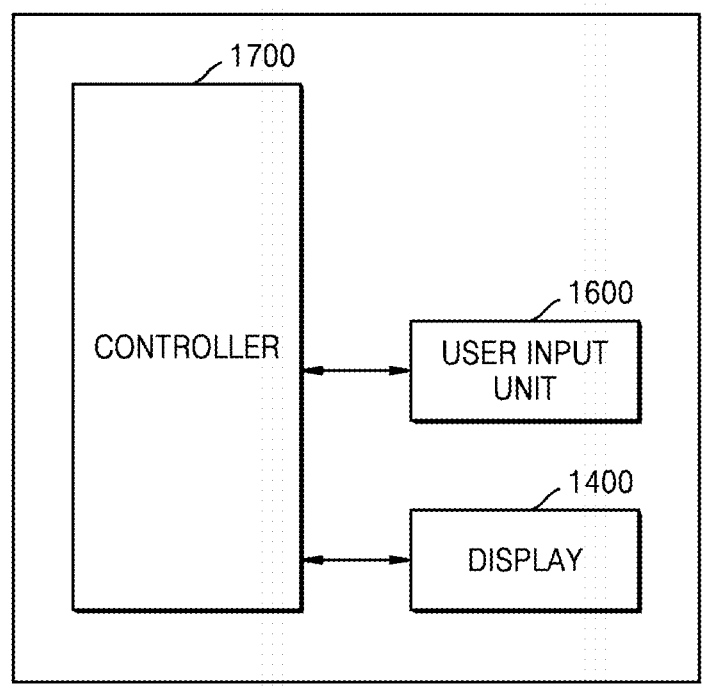
FIG. 17 is a block diagram of a configuration of an ultrasound diagnosis apparatus according to an embodiment.

FIG. 17 is a block diagram of a configuration of the ultrasound diagnosis apparatus 1000 according to an embodiment.

Referring to FIG. 17, the ultrasound diagnosis apparatus 1000 may include a display 1400, a user input unit 1600, and a controller 1700.

However, all of the components shown in FIG. 17 are not essential components. The ultrasound diagnosis apparatus 1000 may include more or fewer components than those shown in FIG. 17.

The display 1400 may display a 2D ultrasound image and a 3D ultrasound image. Furthermore, the display 1400 may display a user interface.

Furthermore, the display 1400 may display a 2D ultrasound image of an object and a 3D ultrasound image with respect to an ROI set in the 2D ultrasound image.

The user input unit 1600 may receive a user input. For example, the user input unit 1600 may receive a user input for setting an ROI in a 2D ultrasound image.

The controller 1700 may control all components of the ultrasound diagnosis apparatus 1000.

Furthermore, the controller 1700 may control the display 1400 to display a region not rendered as a 3D ultrasound image from among regions in a 2D ultrasound image in such a manner that the region is distinguished from a region rendered as the 3D ultrasound image.

Furthermore, the controller 1700 may determine points in a 2D ultrasound image corresponding to a surface of a display volume of an object represented by a 3D ultrasound image.

Furthermore, the controller 1700 may control the display 1400 to display the determined points on the 2D ultrasound image.

Furthermore, the display 1400 may display on a 2D ultrasound image a position of a surface of a display volume of the object represented by a 3D ultrasound image.

Furthermore, the controller 1700 may determine points on the surface of the display volume that intersect a cross-section of the object represented by the 2D ultrasound image as being points in the 2D ultrasound image corresponding to the surface of the display volume.

Furthermore, the controller 1700 may control the display 1400 to display on a 2D ultrasound image a marker indicating a position of a surface of a display volume represented by a 3D ultrasound image.

Furthermore, the display 1400 may display on a 2D ultrasound image a marker indicating a position of a surface of a display volume represented by a 3D ultrasound image. The marker may be a line connecting the determined points in the 2D ultrasound image.

Furthermore, the display 1400 may display a region not rendered as a 3D ultrasound image from among regions in a 2D ultrasound image in such a manner that the region is distinguished from a region rendered as the 3D ultrasound image. For example, the display 1400 may display a region not rendered as the 3D ultrasound image in an ROI set in the 2D ultrasound image as a dot, a line, a plane, a geometrical shape, a color, transparency, a text, or a combination of at least two thereof. Furthermore, the user input unit 1600 may receive a user input for adjusting a depth of a surface of a display volume. After the depth of the surface of the display volume has been adjusted, the controller 1700 may change a position of a marker. In this case, the user input for adjusting a depth of a surface of a display volume may be a user input for changing a 3D rendering parameter necessary for rendering a 3D ultrasound image. Furthermore, the user input for adjusting a depth of a surface of a display volume may be a user input for removing a part of the display volume of the object represented by the 3D ultrasound image.

Furthermore, the display 1400 may display on a 3D ultrasound image a position of a cross-section of an object represented by a 2D ultrasound image.

Furthermore, the user input unit 1600 may receive a user input for setting an ROI in a 2D ultrasound image. The controller 1700 may generate a 3D ultrasound image with respect to the ROI and control the display 1400 to display the generated ultrasound image.

While FIG. 17 shows that the user input unit 1600 is separate from the display 1400, the user input unit 1600 and the display 1400 may be implemented in an integrated form like a touch screen.

Figure 18:
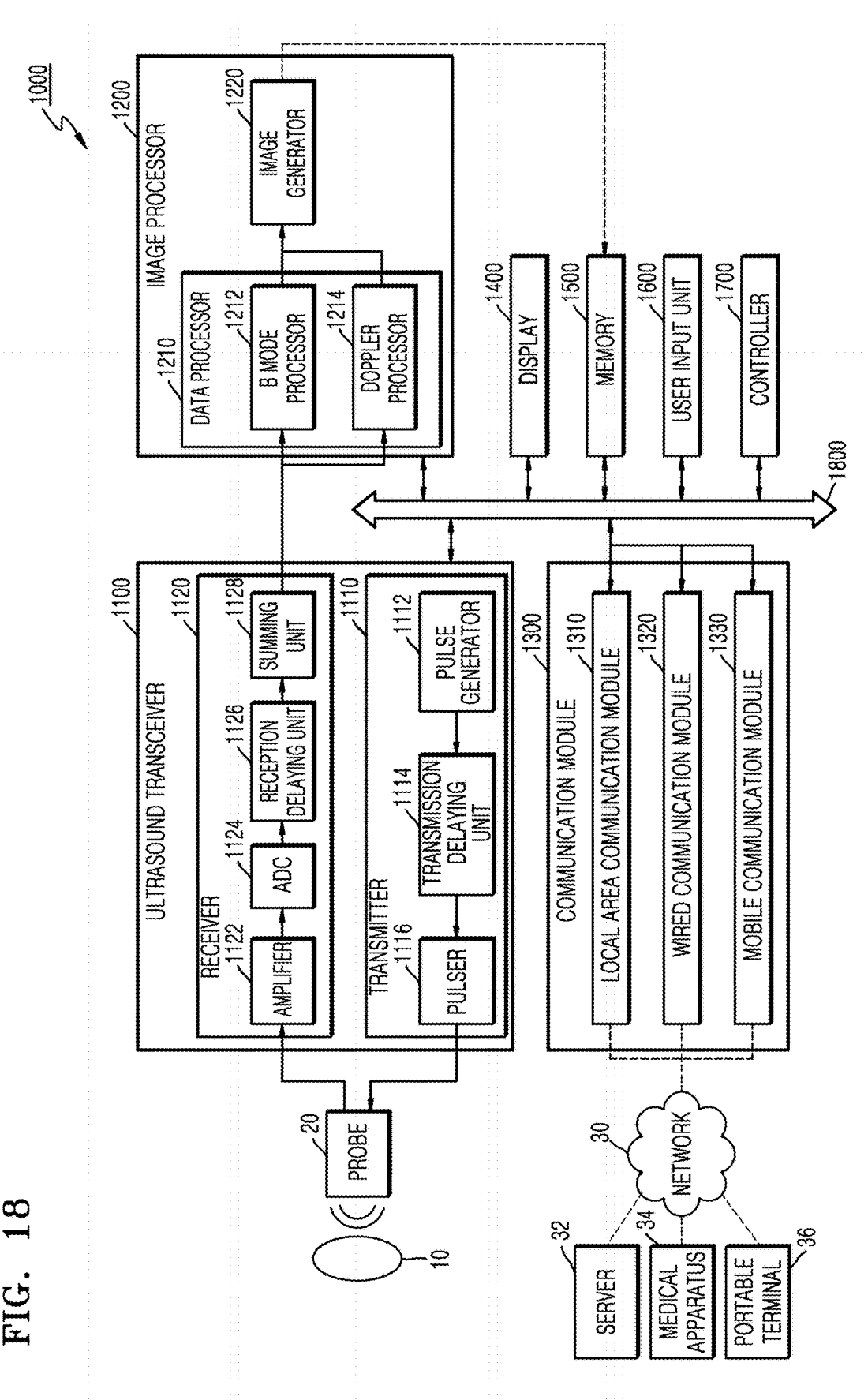
FIG. 18 is a block diagram of a configuration of an ultrasound diagnosis apparatus according to another embodiment.

FIG. 18 is a block diagram of a configuration of an ultrasound diagnosis apparatus 1000 according to another embodiment.

Unlike the ultrasound diagnosis apparatus 1000 of FIG. 17, the ultrasound diagnosis apparatus 1000 according to the embodiment may further include a probe 20, an ultrasound transceiver 1100, an image processor 1200, a communication module 1300, and a memory 1500, which may be connected to one another via a bus 1800.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 124 by delay times necessary for determining reception directionality, and the summing unit 1128 generates ultrasound data by summing the echo signals processed by the reception delaying unit 1166. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 included in a data processor 1210 extracts B mode components from ultrasound data and processes the B mode components. An image generator 1220 may generate an ultrasound image indicating signal intensities as brightness based on the extracted B mode components.

Similarly, a Doppler processor 1214 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to embodiments.

The communication module 1300 is connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc. Furthermore, the ultrasound diagnosis apparatus 1000 may utilize web storage or a cloud server that performs the storage function of the memory 1500 online.

The input device 1600 refers to a means via which a user inputs data for controlling the ultrasound diagnosis apparatus 1000. The input device 1600 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the input device 1600 shown in FIG. 18.

All or some of the probe 20, the ultrasound transceiver 1100, the image processor 1200, the communication module 1300, the display 1400, the memory 1500, the input device 1600, and the controller 1700 may be implemented as software modules. Furthermore, at least one selected from the ultrasound transceiver 1100, the image processor 1200, and the communication module 1300 may be included in the controller 1600. However, embodiments of the present inventive concept are not limited thereto.

Embodiments may be implemented through non-transitory computer-readable recording media having recorded thereon computer-executable instructions such as program modules that are executed by a computer. The non-transitory computer-readable recording media may be any available media that can be accessed by a computer and include both volatile and nonvolatile media and both detachable and non-detachable media. Furthermore, the non-transitory computer-readable recording media may include computer storage media and communication media. The computer storage media include both volatile and nonvolatile and both detachable and non-detachable media implemented by any method or technique for storing information such as computer-readable instructions, data structures, program modules, or other data. The communication media typically embody computer-readable instructions, data structures, program modules, other data of a modulated data signal, or other transmission mechanism, and may include any information transmission media.

Furthermore, in the present specification, the term "unit" may be a hardware component such as a processor or circuit and/or a software component that is executed by a hardware component.

The above description is provided for illustration, and it will be understood by those of ordinary skill in the art that various changes in form and details may be made therein without departing from essential features and the spirit and scope of the present inventive concept as defined by the following claims. Accordingly, the above embodiments and all aspects thereof are examples only and are not limiting. For example, each component defined as an integrated component may be implemented in a distributed fashion. Likewise, components defined as separate components may be implemented in an integrated manner.

The scope of the present inventive concept is defined not by the detailed description thereof but by the appended claims, and all the changes or modifications within the scope of the appended claims and their equivalents will be construed as being included in the present inventive concept.

What is claimed is:

1. An ultrasound diagnosis apparatus comprising:
  a display configured to display a two-dimensional (2D) ultrasound image of an object and a three-dimensional (3D) ultrasound image of a region of interest (ROI) set in the 2D ultrasound image, the 2D ultrasound image and the 3D ultrasound image being displayed separately;
  a controller configured to control the display to display a region not rendered as the 3D ultrasound image from among regions in the 2D ultrasound image in such a manner that the region is distinguished from a region rendered as the 3D ultrasound image; and
  a user input unit configured to receive a user input for removing a part of the display volume of the object represented by the 3D ultrasound image,
  wherein the display is further configured to display the region rendered as the 3D ultrasound image in such a manner as to be distinguished from the region not rendered as the 3D ultrasound image by displaying, on the 2D ultrasound image, points in the 2D ultrasound image corresponding to a surface of a display volume of the object represented by the 3D ultrasound image and from which the part of the display volume is removed based on the user input.

2. The ultrasound diagnosis apparatus of claim 1, wherein the controller is further configured to determine points on the surface of the display volume that intersect a cross-section of the object represented by the 2D ultrasound image as being the points in the 2D ultrasound image corresponding to the surface of the display volume.

3. The ultrasound diagnosis apparatus of claim 1, wherein the display is further configured to display the region rendered as the 3D ultrasound image in such a manner as to be distinguished from the region not rendered as the 3D ultrasound image by displaying the non-rendered region on the 2D ultrasound image.

4. The ultrasound diagnosis apparatus of claim 1, wherein the user input unit is further configured to receive a second user input for adjusting a depth of a surface of a display volume of the object represented by the 3D ultrasound image,
  wherein the controller is further configured to change the non-rendered region as the depth of the surface of the display volume is adjusted and control the display to display the changed non-rendered region.

5. The ultrasound diagnosis apparatus of claim 4, wherein the second user input for adjusting the depth of the surface of the display volume is a user input for changing a 3D rendering parameter necessary for rendering the 3D ultrasound image.

6. The ultrasound diagnosis apparatus of claim 1, wherein the display is further configured to display on the 3D ultrasound image a position of a cross-section of the object represented by the 2D ultrasound image.

7. The ultrasound diagnosis apparatus of claim 1, further comprising a user input unit configured to receive a user input for setting the ROI in the 2D ultrasound image,
  wherein the controller is further configured to generate a 3D ultrasound image based on the set ROI and control the display to display the generated 3D ultrasound image.

8. The ultrasound diagnosis apparatus of claim 1, wherein the controller is further configured to control the display to display points having a same depth as a depth of a starting point of the ROI, from among points in the 2D ultrasound image corresponding to a surface of a display volume of the object, in such a manner that the points having the same depth as the depth of the starting point of the ROI are distinguished from points having depths different from that same depth.

9. The ultrasound diagnosis apparatus of claim 1, wherein the controller is further configured to control the display to display points, each point having a same depth as a depth of a starting point of the ROI, from among points in the 3D ultrasound image corresponding to a cross-section of the object represented by the 2D ultrasound image, in such a manner that the points having the same depth as the depth of the starting point of the ROI are distinguished from points having depths different from that same depth.

10. The ultrasound diagnosis apparatus of claim 1, wherein the 3D ultrasound image is an ultrasound virtual endoscopic image of the ROI set in the 2D ultrasound image, and
  wherein the display is further configured to display a region that has been rendered as the ultrasound virtual endoscopic image from among the regions in the 2D ultrasound image in such a manner that the region is distinguished from a region that has never been rendered as the ultrasound virtual endoscopic image.

11. The ultrasound diagnosis apparatus of claim 1, wherein the controller is further configured to:

determine a line representing a position on the 2D ultrasound image corresponding to a surface of a display volume represented by the 3D ultrasound image; and control the display to distinguish the region not rendered as the 3D ultrasound image from the region rendered as the 3D ultrasound image based on the determined line.

12. A method of displaying an ultrasound image, the method comprising:

displaying a two-dimensional (2D) ultrasound image of an object and a three-dimensional (3D) ultrasound image of a region of interest (ROI) set in the 2D ultrasound image, the 2D ultrasound image and the 3D ultrasound image being displayed separately;

displaying a region not rendered as the 3D ultrasound image from among regions in the 2D ultrasound image in such a manner that the region is distinguished from a region rendered as the 3D ultrasound image; and receiving a user input for removing a part of the display volume of the objected represented by the 3D ultrasound image, wherein the displaying of the region not rendered as the 3D ultrasound image in such a manner as to be distinguished from the region rendered as the 3D ultrasound image comprises displaying, on the 2D ultrasound image, points in the 2D ultrasound image corresponding to a surface of a display volume of the object represented by the 3D ultrasound image and from which the part of the display volume is removed based on the user input.

13. The method of claim 12, wherein the displaying of the points in the 2D ultrasound image corresponding to the surface of the display volume of the object represented by the 3D ultrasound image comprises determining points on the surface of the display volume that intersect a cross-section of the object represented by the 2D ultrasound image as being the points in the 2D ultrasound image corresponding to the surface of the display volume.

14. The method of claim 12, wherein the displaying of the region not rendered as the 3D ultrasound image in such a manner as to be distinguished from the region rendered as the 3D ultrasound image comprises displaying the non-rendered region on the 2D ultrasound image.

15. The method of claim 12, further comprising:

receiving a second user input for adjusting a depth of a surface of a display volume of the object represented by the 3D ultrasound image; and changing the non-rendered region as the depth of the surface of the display volume is adjusted and displaying the changed non-rendered region.

16. The method of claim 15, wherein the second user input for adjusting the depth of the surface of the display volume is a user input for changing a 3D rendering parameter necessary for rendering the 3D ultrasound image.

17. The method of claim 12, further comprising displaying on the 3D ultrasound image a position of a cross-section of the object represented by the 2D ultrasound image.

18. The method of claim 12, further comprising:

receiving a user input for setting the ROI in the 2D ultrasound image;

generating a 3D ultrasound image based on the set ROI; and displaying the generated 3D ultrasound image.

19. The method of claim 12, further comprising displaying points having a same depth as a depth of a starting point of the ROI, from among points in the 2D ultrasound image corresponding to a surface of a display volume of the object, in such a manner that the points having the same depth as the depth of the starting point of the ROI are distinguished from points having depths different from that same depth.

20. The method of claim 12, further comprising displaying points, each point having a same depth as a depth of a starting point of the ROI, from among points in the 3D ultrasound image corresponding to a cross-section of the object represented by the 2D ultrasound image, in such a manner that the points having the same depth as the depth of the starting point of the ROI are distinguished from points having depths different from that same depth.

21. The method of claim 12, wherein the 3D ultrasound image is an ultrasound virtual endoscopic image of the ROI set in the 2D ultrasound image, the method further comprising displaying a region that has been rendered as the ultrasound virtual endoscopic image from among the regions in the 2D ultrasound image in such a manner that the region is distinguished from a region that has never been rendered as the ultrasound virtual endoscopic image.

22. The method of claim 12, further comprising:

determining a line representing a position on the 2D ultrasound image corresponding to a surface of a display volume represented by the 3D ultrasound image; and controlling the display to distinguish the region not rendered as the 3D ultrasound image from the region rendered as the 3D ultrasound image based on the determined line.

* * * * *